United States Patent
Punchard et al.

(10) Patent No.: US 10,808,214 B2
(45) Date of Patent: Oct. 20, 2020

(54) LIGHT EMITTING DIODE PHOTOBIOREACTORS AND METHODS OF USE

(71) Applicant: Avespa Corporation, Jupiter, FL (US)

(72) Inventors: David Punchard, Hollywood, FL (US); Philippe Bois, Jupiter, FL (US); Angela Cortina Burgueno, Salamanca (ES)

(73) Assignee: Avespa Corporation, Jupiter, FL (US)

( * ) Notice: Subject to any disclaimer, the term of this patent is extended or adjusted under 35 U.S.C. 154(b) by 0 days.

(21) Appl. No.: 16/280,165

(22) Filed: Feb. 20, 2019

(65) Prior Publication Data

US 2019/0185796 A1 Jun. 20, 2019

Related U.S. Application Data

(60) Division of application No. 15/416,989, filed on Jan. 26, 2017, now Pat. No. 10,246,674, which is a
(Continued)

(51) Int. Cl.
*C12N 1/12* (2006.01)
*C12M 1/00* (2006.01)
(Continued)

(52) U.S. Cl.
CPC ............ *C12M 21/02* (2013.01); *C12M 27/00* (2013.01); *C12M 29/06* (2013.01); *C12M 29/26* (2013.01);
(Continued)

(58) Field of Classification Search
None
See application file for complete search history.

(56) References Cited

U.S. PATENT DOCUMENTS

| 5,104,803 A | 4/1992 | Delente |
| 5,846,816 A | 12/1998 | Forth |

(Continued)

FOREIGN PATENT DOCUMENTS

| CN | 101580796 A | 11/2009 |
| CN | 202007224 | 10/2011 |

(Continued)

OTHER PUBLICATIONS

Jacobi, A. et al., Advanced photobioreactor LED illumination system: Scale-down approach to study microalgal growth kinetics, Eng. Life Sci. 2012, 12, No. 6, 621-630.
(Continued)

*Primary Examiner* — Allison M Fox
*Assistant Examiner* — Qing Xu
(74) *Attorney, Agent, or Firm* — BakerHostetler

(57) ABSTRACT

A photobioreactor system and a process for its use is illustrated, whereby water and nutrients from multiple sources are balanced (mixed using aeration) to the specific requirements of the particular photosynthetic organism strain used, sterilized, further mixed to balance the system and seeded with the photosynthetic microorganism, e.g. microalgae (dilution of a concentrated stock or added to an existing algal biomass). In accordance with such an embodiment, the algal biomass is then grown for a most efficient number of hours in a totally controlled environment where temperature (using aeration, an internal coil cooling system, or a combination thereof), pH (via $CO_2$ delivery) and light delivery (using internal lighting directly inside the algal biomass) are optimized to the algal strain grown.

7 Claims, 12 Drawing Sheets

Related U.S. Application Data continuation-in-part of application No. PCT/US2016/044796, filed on Jul. 29, 2016.

(60) Provisional application No. 62/198,652, filed on Jul. 29, 2015.

(51) Int. Cl.
  *C12M 1/02* (2006.01)
  *C12M 1/12* (2006.01)
  *F21V 8/00* (2006.01)

(52) U.S. Cl.
  CPC ............ *C12M 31/10* (2013.01); *C12M 37/00* (2013.01); *C12N 1/12* (2013.01); *G02B 6/0068* (2013.01); *G02B 6/0078* (2013.01); *G02B 6/0085* (2013.01)

(56) References Cited

U.S. PATENT DOCUMENTS

| | | |
|---|---|---|
| 8,569,050 B1 | 10/2013 | Ericsson |
| 8,716,010 B2 | 5/2014 | Csanyi et al. |
| 2009/0047722 A1 | 2/2009 | Wilkerson et al. |
| 2010/0028977 A1 | 2/2010 | Ng et al. |
| 2010/0255458 A1 | 10/2010 | Kinkaid |
| 2010/0267122 A1 | 10/2010 | Chinnasamy et al. |
| 2010/0323436 A1 | 12/2010 | Lee et al. |
| 2012/0149091 A1 | 6/2012 | Wilkerson et al. |
| 2012/0270304 A1 | 10/2012 | Johnson |
| 2012/0288921 A1 | 11/2012 | Yuan et al. |
| 2013/0023044 A1 | 1/2013 | Gleason |
| 2013/0102069 A1 | 4/2013 | Neeb et al. |
| 2014/0073035 A1 | 3/2014 | Friederich et al. |
| 2014/0212954 A1 | 7/2014 | Auner et al. |
| 2014/0286043 A1 | 9/2014 | Sykora et al. |
| 2015/0118735 A1 | 4/2015 | Ganuza et al. |
| 2015/0140642 A1 | 5/2015 | Ohtake et al. |
| 2015/0299630 A1 | 10/2015 | Roulston |

FOREIGN PATENT DOCUMENTS

| | | |
|---|---|---|
| CN | 104152344 A | 11/2014 |
| CN | 105087371 A | 11/2015 |
| WO | WO 2010-115655 A1 | 10/2010 |
| WO | WO 2014-006551 A1 | 1/2014 |
| WO | WO 2015-087169 A2 | 6/2015 |

OTHER PUBLICATIONS

Lee, C.G., et al., High-Density algal Photobioreactors using Light-Emitting Diodes, Biotechnology and Bioengineering, vol. 44, 1994, pp. 1161-1167.

Olivieri, G. et al., Advances in photobioreactors for intensive microalgal production: configurations, operating strategies and applications, J Chem Technol Biotechnol, 2014; 89: 178-195.

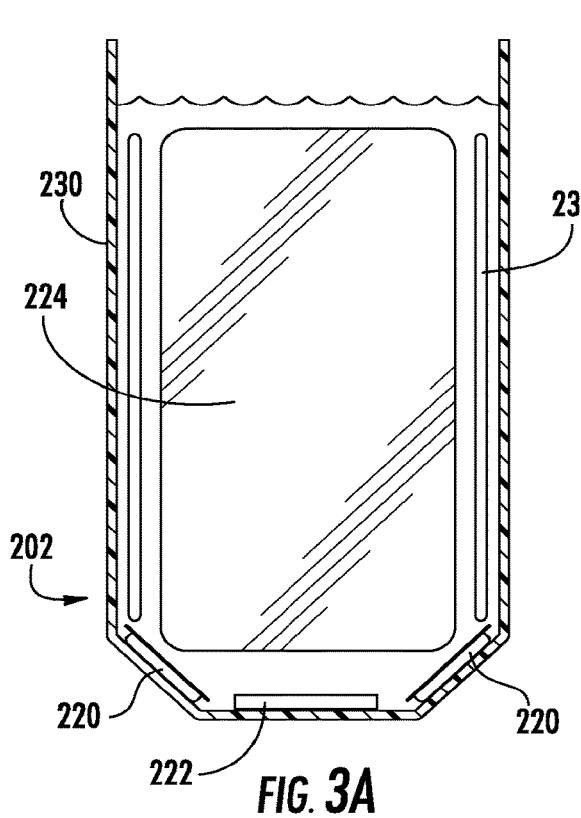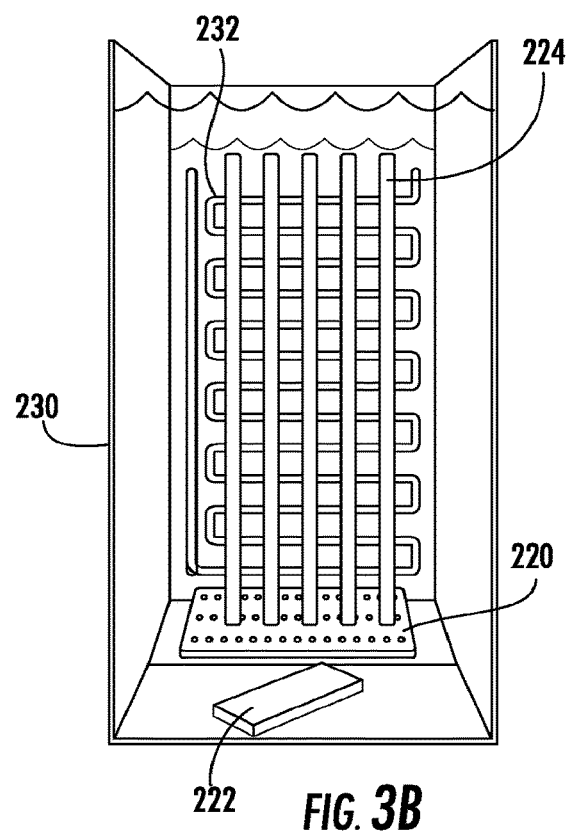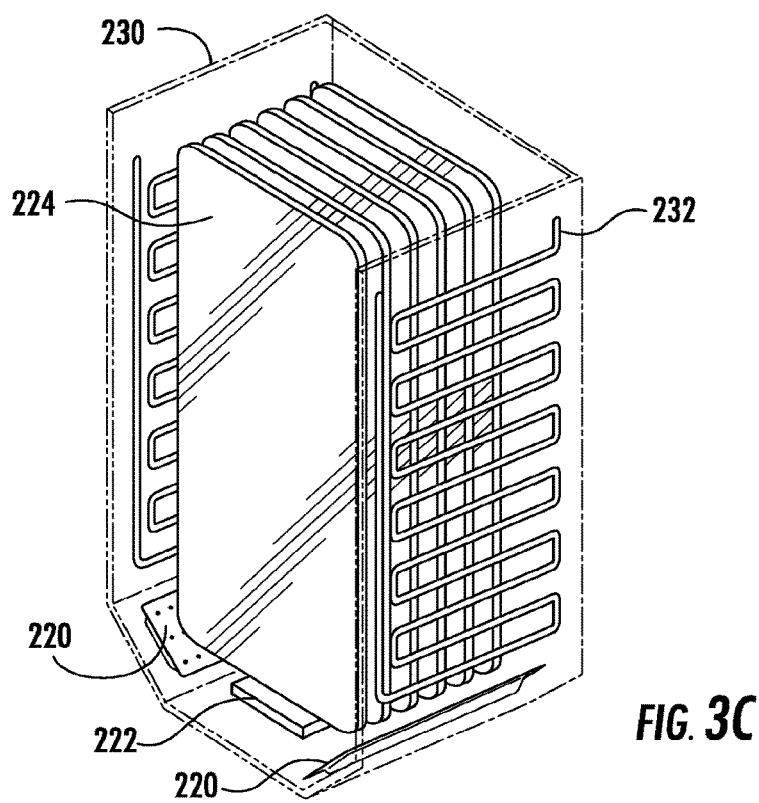

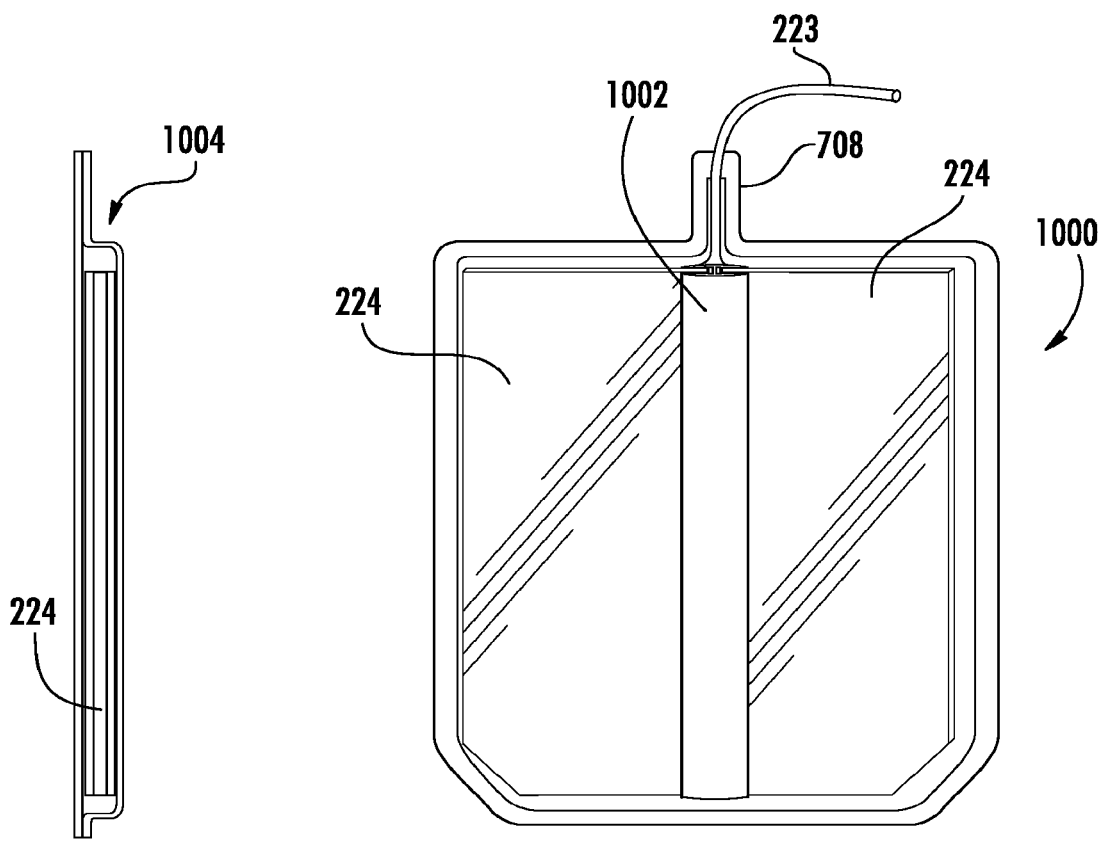
FIG. 10A
FIG. 10B
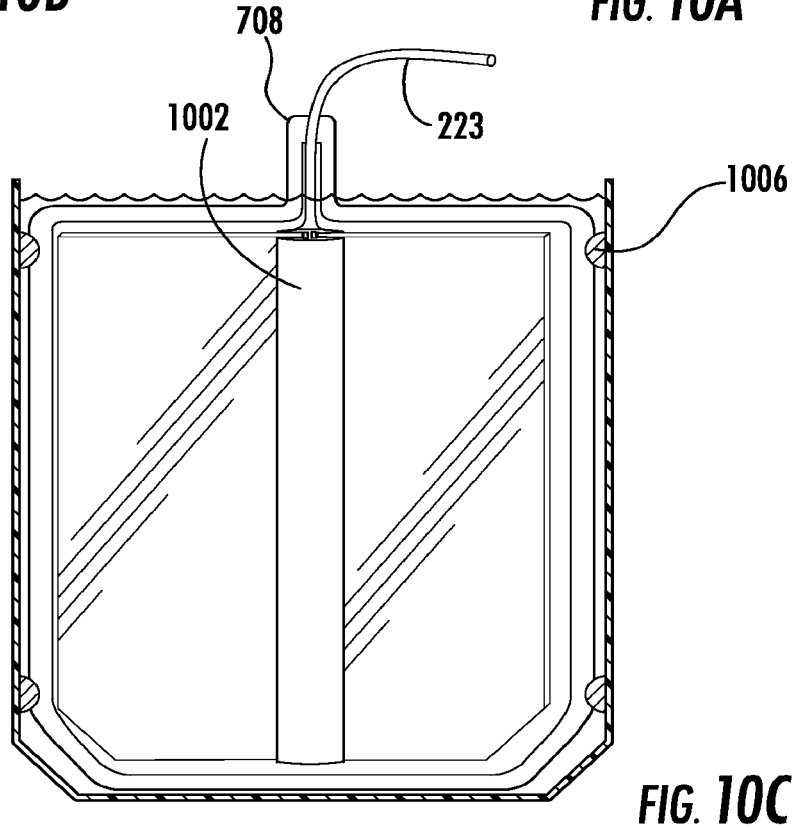
FIG. 10C

LIGHT EMITTING DIODE PHOTOBIOREACTORS AND METHODS OF USE

CROSS REFERENCE TO RELATED APPLICATIONS

This patent application is a divisional of now-allowed U.S. patent application Ser. No. 15/416,989 (filed Jan. 26, 2017), which is a continuation-in-part of PCT/US2016/044796 (filed Jul. 29, 2016), which claims priority to U.S. Provisional Patent Application No. 62/198,652 (filed Jul. 29, 2015), the entirety of each of which applications is incorporated by reference herein in its entirety for any and all purposes.

FIELD OF THE INVENTION

The present invention is directed toward a bioreactor system for optimizing the cultivation and harvesting of photosynthetic organisms. The invention particularly relates to bioreactor systems which are essentially self-contained modular scalable units that maintain all critical parameters, such as the levels of carbon dioxide, oxygen, water, nutrients, temperature, biomass suspension and light energy necessary for the optimal preparation, growth and harvesting of such photosynthetic organisms. The invention more particularly relates to a system of bioreactors which have photoreactor capability, whereby they are designed to include a radiation source, preferably a light emitting diode (LED) array, to emit light within the bioreactors of a particular wavelength, which wavelength has been selected for optimal growth and harvesting of a particular species of photosynthetic organism. It is designed for long term culture of micro-algal biomass in a semi-continuous manner so as to permanently produce the algal biomass while protecting and preserving the integrity of the organism grown.

BACKGROUND OF THE INVENTION

Photosynthesis is a process used by plants and other organisms (i.e., protists and cyanobacteria) to convert light energy into chemical energy that can be later released to fuel the organisms' activities. This chemical energy is stored in carbohydrate molecules, such as sugars, which are synthesized from carbon dioxide and water. In most cases, oxygen is also released as a waste product. Most plants, most algae, and cyanobacteria perform photosynthesis; such organisms are called photoautotrophs. Although photosynthesis is performed differently by different species, the process always begins when energy from light is absorbed by proteins called reaction centres that contain green chlorophyll pigments. In plants, these proteins are held inside organelles called chloroplasts, which are most abundant in leaf cells, while in bacteria they are embedded in the plasma membrane. In these light-dependent reactions, some energy is used to strip electrons from suitable substances, such as water, producing oxygen gas while fixing carbon molecules from $C_2$. Furthermore, two further compounds are generated: reduced nicotinamide adenine dinucleotide phosphate (NADPH) and adenosine triphosphate (ATP), which provide energy to cells.

In plants, algae and cyanobacteria, sugars are produced by a subsequent sequence of light-independent reactions called the Calvin cycle, but some bacteria use different mechanisms, such as the reverse Krebs cycle. In the Calvin cycle, atmospheric carbon dioxide is incorporated into already existing organic carbon compounds, such as ribulose bisphosphate. Using the ATP and NADPH produced by the light-dependent reactions, the resulting compounds are then reduced and removed to form further carbohydrates, such as glucose.

Photoreactors, in particular photobioreactors, are known, and have been used for the industrial production of microalgae, for example *Chlorella* sp, *Chlamydomonas* sp or *Haematococcus pluvialis*, photosynthetic bacteria such as for example cyanobacteria (e.g., *Arthrospira, Rhodobacter, Rhodospirillum*), mosses or other plant cell cultures.

Open channel photobioreactors, such as ponds, experience difficulties from contamination by other photosynthetic organisms, parasites, predators or external pollutants and from the inefficient use of light that illuminates only the top portion of the pond. More efficient photobioreactors will have an illumination surface area per unit volume (S/V) ratio that is high, shallow ponds are the norm. This, however, greatly increases land space requirements for pond-based photobioreactors. In addition, when these ponds use natural sunlight the process is limited by the available hours of sunlight. Such processing limitations can be important if the photobioreactors are used to process waste gasses from polluting facilities that operate twenty-four hours a day. Further, if these ponds are not insulated from the elements such as seasonal changes in weather, the photosynthetic organisms will find it difficult to withstand changes in temperature, external pollution, and attack from hostile species. Other limitation found in open ponds and raceways is the inefficient mixing, that leads to low productivities due to low mass transfer of gasses such as $CO_2$ that limits the growth or oxygen that, inhibits the growth. Lack of control and laminar flows end in sedimentation of the cultures and biofouling, decreasing productivity and increasing maintenance and production costs.

An alternative technology that has received considerable attention is the closed channel system such as those systems having cylindrical tubes that employ the airlift principle. In general, airlift photobioreactors have photosynthetic material such as algae suspended in a liquid medium into which air or gas is injected into the bottom of the system, which then rises through the fluid medium in the cylindrical tube. Conventional airlift photobioreactors, however, suffer from the lack of easily definable flow patterns that can be duplicated or controlled. It is further known to provide an apparatus for culturing photosynthetic microorganisms having at least one bioreactor and at least one source of electromagnetic radiation wherein the at least one source of electromagnetic radiation is a light emitting diode.

One of the key industry drivers for the development of this technology has been the need to produce biofuels as a substitute for fossil fuels, as clearly stated by Germany's Fraunhofer Institute for Interfacial Engineering and Biotechnology "currently biofuels are mainly produced from plant-based raw materials for example biodiesel from rapeseed or palm oil. In Germany the arable land will no longer be available for food production; in Southeast Asia rainforests are being cleared for oil palm plantations. The high water consumption during the cultivation of land plants for the production of biofuels is also viewed critically. Moreover, the current production capacity and area available for this purpose cannot meet the demand for renewable resources for biofuels". Therefore, despite a century of commercial algal research encompassing many aspects of the value chain (e.g., biology, open pond, closed bio-reactors, bioreactor design, extraction), to date a commercially viable solution has not been reduced to practice that can address the publicly agreed challenges and can meet the market need for large volumes of high quality biomass.

DESCRIPTION OF THE PRIOR ART

U.S. Published Patent Application 2010/0190227 to Dauth et al. relates to a photoreactor comprising LED plastic molded parts, preferably LED silicone molded parts, optionally in combination with light-guide molded parts as a radiation source; in particular, photobioreactors comprising LED plastic molded parts, preferably LED silicone molded parts, optionally in combination with light-guide molded parts as a radiation source.

U.S. Pat. No. 6,602,703 to Dutil, describes a photobioreactor having a container for containing a liquid culture medium for cultivating photosynthetic organisms, a plurality of parallel light-emitting tubes mounted within the container and extending in a first direction, and having an outer surface; and cleaning means mounted within the container for cleaning the outer surface of the light-emitting tubes.

U.S. Pat. No. 8,476,067 to Morgan discloses a photobioreactor having a generally vertical fluidic pathway and a generally vertical helically shaped fluidic pathway. The two fluidic pathways are fluidly connected by a head cap assembly and a base assembly such that a biologically active material is able to move fluidly, without substantial impediment, back and forth between the generally vertical fluidic pathway and the generally vertical helically shaped fluidic pathway. A light source, which may be a light emitting diode (LED), is at least partially positioned inside a portion of the generally vertical helically shaped fluidic pathway. This light source can comprise a plurality of light emitting diodes (LEDs). Further, the wavelengths emitted from the light source may be in the range of visible light, more particularly, between about 400 to about 700 nm.

WO 2008/151376 to Stroud is directed toward an apparatus for culturing photosynthetic microorganisms comprising at least one bioreactor and at least one source of electromagnetic radiation wherein the at least one source of electromagnetic radiation is a light emitting diode comprising an organic or polymeric emissive layer.

U.S. Published Patent Application 2012/0270304 discloses a photo-bioreactor (PBR) system using a plurality of light-emitting panels and buoyancy-driven channel flow. There is a disclosure of internally illuminated light emitting diode (LED) panels and two-sided light emitting panels, using sheets of diodes combined with solar panels and collectors.

U.S. Published Patent Application 2012/0149091 discloses a bioreactor for cultivating photosynthetic organisms. There is a disclosure of LEDs and two-sided light emitting panels. These are internal LED illuminated PBRs utilizing sheets of diodes combined with solar collectors and fiber optics.

WO 2015/087169A2 discloses a photobioreactor for culturing phototrophic microorganisms having a framework supporting a plurality of horizontally oriented, vertically spaced shelves. This is an externally illuminated PBR with an open design, and is fundamentally different than the highly controlled platform of the instantly disclosed invention.

U.S. Published Patent Application 2013/0023044 discloses an algae bioreactor and biofuel production system utilizing multiple LEDs (rod configuration) (Paragraphs [0008], [0025], [0046], and [0052]).

U.S. Published Patent Application 2010/0323436 discloses a photobioreactor using light emitting diodes arranged as flat plates (FIG. 3). LED illuminated PBR external and internal using sheets of light (OLED), LED sheets are used rather than light guides.

U.S. Published Patent Application 2013/0102069 discloses a bioreactor for growing algae having light generated by LEDs. The method includes emitting light by the light emitting diode having a first refractive index, transferring the light through a liquid medium having a second refractive index, and a solid medium having a third refractive index, into the aqueous liquid having a fourth refractive index.

Chinese Publication CN 105087371A discloses a photobioreactor for automatically culturing microalgae using an LED light source array. In this reference, the LED lighting is external and limited; scaling up appears to be limited.

U.S. Published Patent Application 2014/0073035 relates to a photobioreactor intended for the continuous culture of photosynthetic microorganisms, comprising at least one culture enclosure (1) intended to contain the microorganism culture medium (3) and at least one light source (2) outside the culture enclosure (1), characterized in that it further comprises at least one cylindrical or prismatic light diffusion element (4) placed inside the culture enclosure (1), the light diffusion element (4) being coupled optically with the light source (2) so as to collect the photons emitted by the light source (2) and to return them to the culture medium (3) by its lateral surface. See FIG. 6.

U.S. Published Patent Application 2015/0140642 discloses a method of culturing green algae using LEDs. The application describes a way to increase and favor the growth of green stage *Haematococcus pluvialis* by using a combination of external red and blue light.

These prior art methods and systems for the cultivation of photosynthetic organisms do not teach or suggest the elements necessary for providing optimal conditions for the growth and harvesting of photosynthetic organisms, such as microalgae, and do not appear to be scalable for commercial operations. The prior art does not contemplate the required apparatus, nor the methodology requisite to achieving the algal growth exemplified by the presently disclosed invention.

What is lacking in the art is a commercially highly scalable viable system and methodology, capable of delivering high yields of biomass from a universal approach adaptable to any biologically suitable media or light dependent organism, that could be used anywhere in the world regardless of external lighting or environmental conditions. The system must be a sterile, closed, scalable system, designed to accommodate ever-changing production requirements. In addition, it should be designed with commercial usage in mind and provide for easy access, handling and cleaning capability without cumbersome and complex hardware.

SUMMARY OF THE INVENTION

The present invention is directed toward a photobioreactor system and a process for its use whereby water and nutrients from multiple sources are balanced (mixed using aeration) to the specific requirements of the particular photosynthetic organism strain used, sterilized, further mixed and brought to the optimal temperature to balance the system and seeded with the photosynthetic microorganism, e.g. microalgae (dilution of a concentrated stock or added to an existing algal biomass). In accordance with such an embodiment, the algal biomass is then grown for a most efficient number of hours in a totally controlled environment where biomass suspension (using air injected in the tank using bubblers), temperature (using an internal coil cooling system), pH (via $CO_2$ delivery) and light delivery (using internal lighting directly inside the algal biomass) are optimized to the algal strain grown. At the end of a given growth period, semi-continuous harvesting is performed where a fraction of the algal biomass (e.g. about 10-50%) is harvested and replaced by fresh medium, the remaining biomass, about 50-90%, being used to seed the next growth phase.

The invention further relates to methods of treating waste materials using bioreactors and methods of isolation and subsequent manufacture of desired substances using bioreactors and the photosynthetic biomass, e.g., algal biomass, produced from such devices. The devices and methods of the present invention promise to generate at least 5 to 50 times the amount of biomass by a combination of the absolute biomass weight for an equal amount of reactor volume, the energetic efficiency of the system where less energy is required to produce an equal or higher amount of biomass and with the ability to harvest more biomass over an equal period of time. In an embodiment the photobioreactor has at least one vessel for holding the growth medium, a light source that must be immersed in the vessel, a means for circulating the media efficiently, a means for removing biomass, and a means to monitor relevant parameters such as temperature and/or pH. In addition, the photobioreactor contains a means to deliver $CO_2$ (e.g., fine bubble ceramic diffuser).

In an embodiment, the invention may be formed as a group of reactor vessels in fluidic engagement with at least one vessel for replacement media (designated a firewall vessel) and at least one harvest tank vessel. Sufficient valving is provided to enable isolation of the individual vessels and to alternatively and individually bring them into fluidic engagement with at least one firewall and at least one harvest vessel, as needed. All connective hardware can be readily rinsed, sterilized and flushed in order to limit contamination. The bottom of the reactor vessel contains at least one bubbler connected to a source of air sufficient to operate the bubbler in which bubbles produce currents, which circulate the medium and microalgae. Optionally, the vessel contains a second bubbler for the introduction of gasses such as $CO_2$ (carbon dioxide) into the medium. Lights comprising thin and substantially flat light guides powered by LEDs are arranged vertically in the vessel, preferably in arrays to maximize homogeneous light distribution yet providing sufficient turbulence in order to maximize algal biomass suspension, exposure to light, and oxygen venting.

In an embodiment, the invention teaches a method of culturing microalgae in which the reactor vessels are filled with medium and a starter microalgae solution and exposed to sufficient light to allow the microalgae to grow at a rate such that they may be harvested in a semi-continuous manner, thereby ensuring that a given percentage of the algal biomass is drained and harvested every day and replaced by the same amount of nutrient rich medium in the most efficient possible way.

In an alternative embodiment, continuous growth of biomass is provided by flowing the biomass containing media through a series of vessels or through a single long vessel, which may optionally be partitioned to control flow.

In an embodiment, the bioreactor designs of the present invention allow for harvesting from about 10% to about 50% of the bioreactor vessel each day allowing harvesting of the full vessel every 2-10 days. The harvested biomass is generally at a density of three to ten times based on dry weight that of conventional systems. As such the present invention can achieve efficiencies as great as 100 times that of conventional systems by not only producing higher biomass concentration with a higher energetic efficiency but also by harvesting more often when compared to a batch growth methodology.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

FIGS. 3A, 3B and 3C illustrate the modular nature of the design by showing a basic unit consisting of light panels, an aeration system, a $CO_2$ delivery diffuser and a cooling system;

FIGS. 10A, 10B, and 10C, illustrate a front view and side view of an alternative design for a light guide, as well as a sectional view of such a guide inserted in a vessel (10C);

DETAILED DESCRIPTION OF ILLUSTRATIVE EMBODIMENTS

In one embodiment the present invention includes at least one vessel for holding the growth medium, a light source which is immersed in the vessel, a means for circulating the media, and a means for removing the biomass. Optionally, vessels for collecting harvested biomass, vessels for accommodating an optional stress phase, and vessels for refilling the system, so-called firewall vessels, may be provided.

Figure 1:
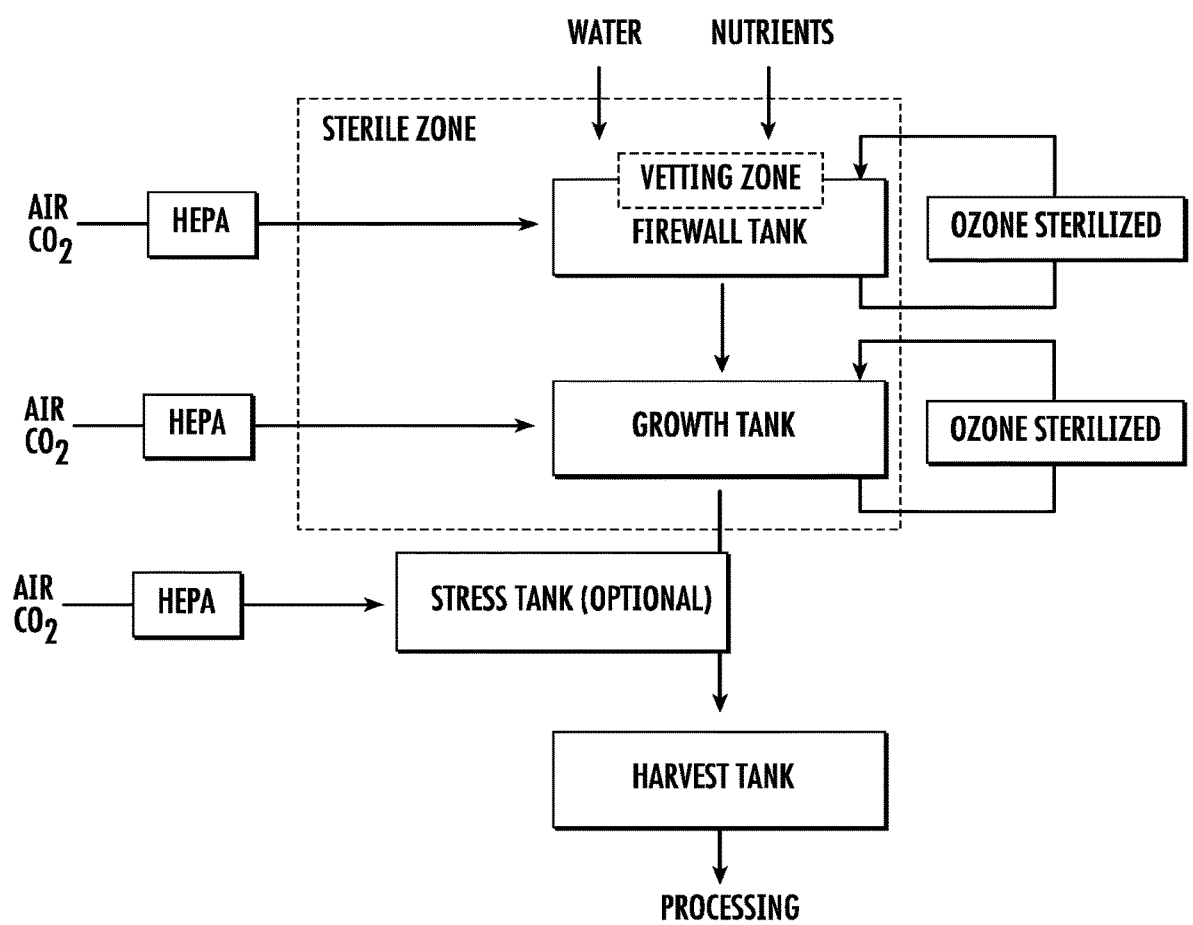
FIG. 1 is a flow-chart for a simplified continuous algal growth model including a firewall containing highly controlled input sources to the system, a growth phase, an optional stress phase and a harvest phase.

With reference to FIG. 1, a flow-chart for a simplified continuous growth model is illustrated having a firewall containing highly controlled input sources to the system, a growth phase, an optional stress phase and a harvest phase. Continuous growth requires a vetting upstream process that guarantee that every component coming into the system is balanced, sterile and optimized for every given alga strain. The system has the ability to be sterilized by a plurality of means (i.e., ozone, steam, chemical) whereby every fundamental portion of the process, from an individual tank (firewall, growth) or any and all connective fluidic pathways effective to interconnect the various components of the growth and harvesting assembly (water, air). This provides an ability to contain and eliminate any potential biological and, to some extent, chemical contaminants.

Figure 2A:
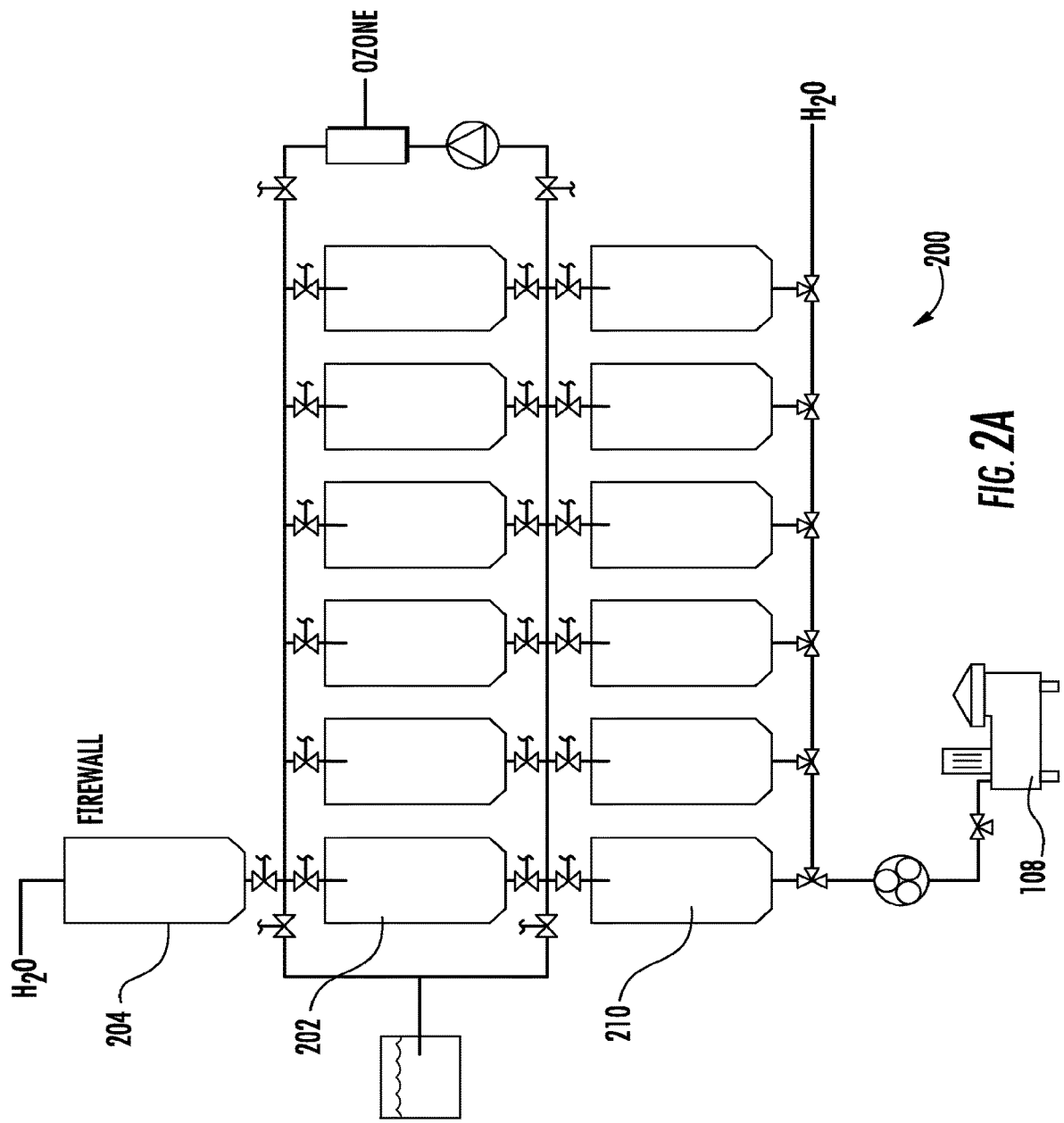
FIG. 2A is an illustrative embodiment of a vertically disposed algal growth and harvesting assembly.

Now referring to FIG. 2A, an alternative embodiment of an algal growth and harvesting reactor vessel assembly 200 is illustrated wherein the vessels may be arranged in a vertical stacked relationship, whereby the firewall mixing/sterilizing tank vessel assemblies 204, which serve as storage vessels, are located at the top of the rack, and feed the growth tank vessel assemblies by gravity. This embodiment is characterized by specific groups of reactor vessel assemblies, more or less vertically disposed and arranged with respect to one another, and fluidically coupled for gravity flow from one group of said reactor vessel assemblies to another. More specifically, in this embodiment, one or more uppermost firewall tank vessel assemblies (storage vessels) 204, which contain a source of sterile, temperature regulated water and a source of nutrient replenishment, are situated in fluidic engagement for gravity flow into a plurality of growth tank vessel assemblies 202. Growth tank vessel assemblies 202 are constructed and arranged to periodically flow into the lowermost harvest/stress tank vessel assemblies 210. It is emphasized, that when an optional stress phase is included, the stress phase may occur in one or more of the harvest tanks. These harvest/stress tanks are constructed and arranged to further accommodate at least one light panel assembly 700 (as particularly described in relation to FIGS. 7A, 7B, 7C and 7D), containing at least one edge-fed light guide assembly, the edge-fed light guide assembly containing at least one edge-fed two-sided light guide, at least one light-emitting diode (LED) strip and at least one heatsink, wherein the at least one edge-fed two-sided light guide and the at least one LED strip are maintained in juxtaposed relation within the heatsink whereby light emitted from the at least one LED strip is injected into the two-sided light guide and is uniformly distributed from each side thereof. Sufficient alternative fluidic coupling devices (not shown) are provided to enable isolation of any individual reactor vessel assembly (202, 204 or 210) and to enable releasable fluidic engagement with the firewall vessel assemblies 204 for preparation of replacement medium and with harvest/stress tank vessel assemblies 210 as required.

Figure 4:
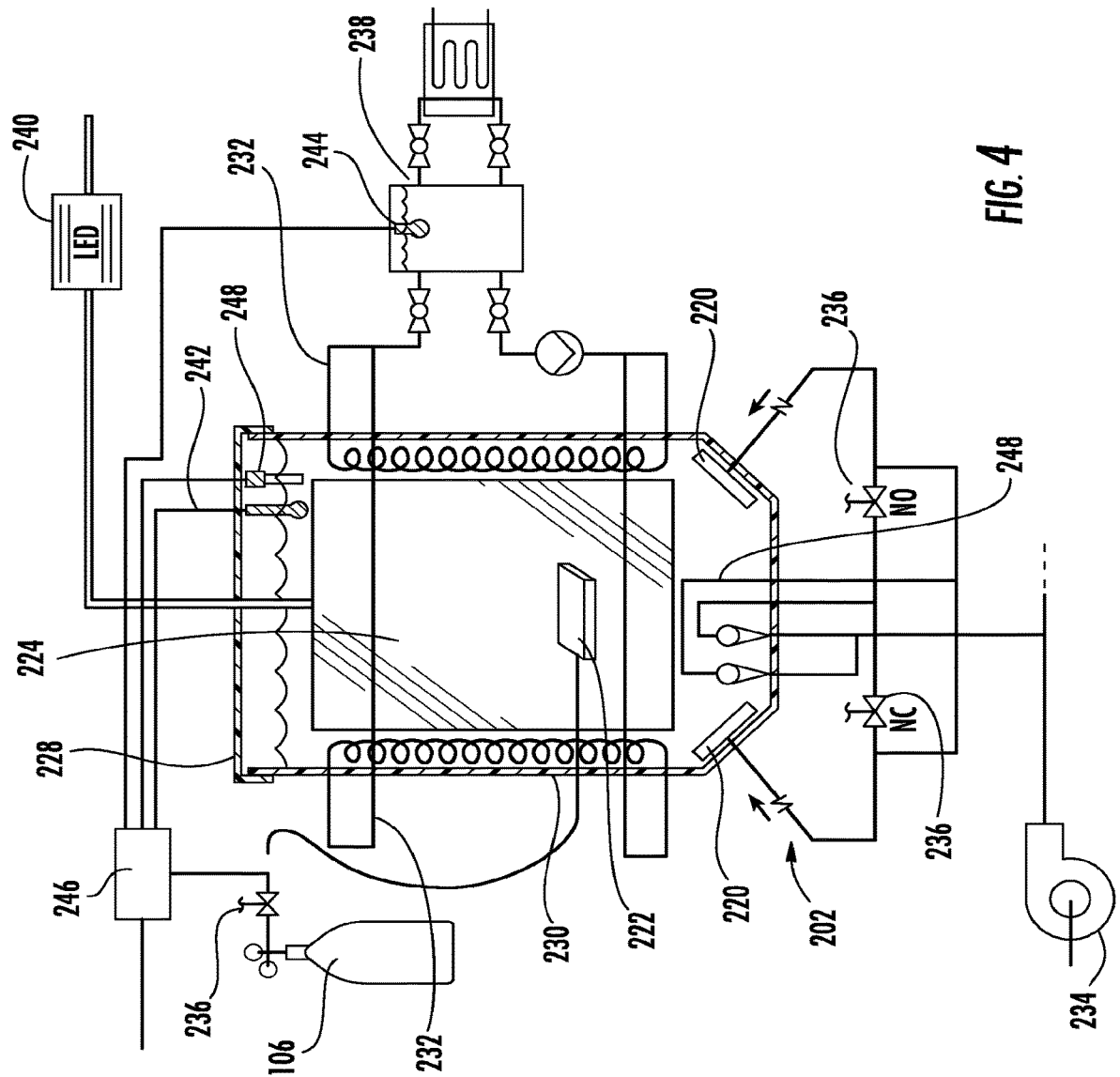
FIG. 4 is an engineering schematic of the elements that are required for a basic module to be functional.

As taught in the embodiment illustrated by FIG. 4, a source of compressed $CO_2$ 106 is provided, and the biomass is harvested by use of a centrifugation biomass collection station 108.

Figure 2B:
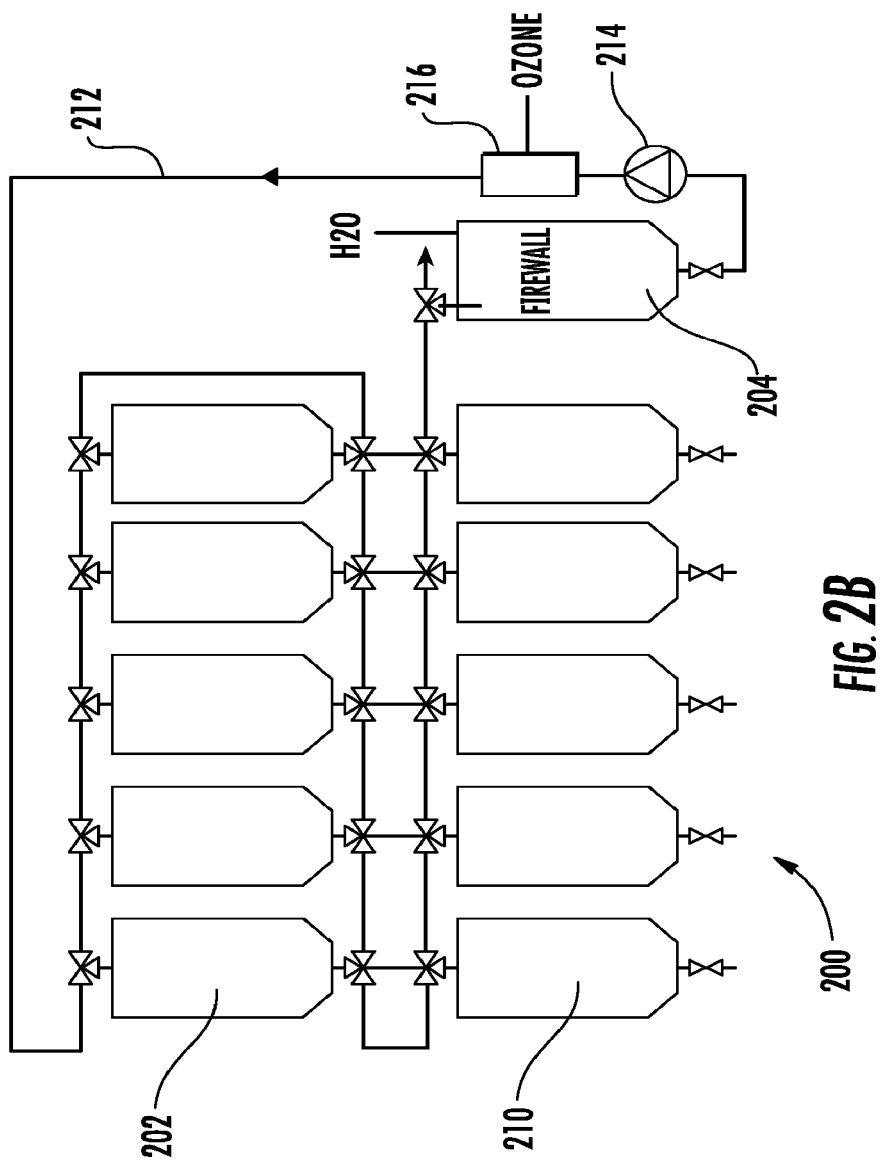
FIG. 2B is an illustrative embodiment of an algal growth and harvesting assembly inclusive of a system to provide constant flow-through of a sterile water supply to all connective fluidic pathways effective to interconnect the various components of the growth and harvesting assembly.

With further reference to FIG. 2B, an illustrative alternative embodiment of an algal growth and harvesting assembly 200, as shown in FIG. 2A, is shown. This embodiment further includes a system to provide constant flow-through of a sterile water and nutrient supply from firewall mixing/sterilizing tank vessel assembly 204 to a plurality of connective fluidic pathways 212 which are constructed and arranged so as to be effective to interconnect the various components of the growth tank vessel assembly 202 and harvest tank vessel assembly 210. In this embodiment, the firewall mixing/sterilizing tank vessel assemblies 204 need not be arranged for gravity flow to the growth tank vessel assemblies 202.

The system to provide constant flow-through of a sterile water and nutrient supply includes a plurality of connective fluidic pathways 212 which are constructed and arranged so as to be effective to interconnect the various components of the growth tank vessel assembly 202 and harvest tank vessel assembly 210 a circulating pump 214, which provides constant flow, and a source of a sterilant, illustrated by, albeit not limited to ozonator 216. This system functions to maintain a pressurized flow of sterile water and nutrients through the connective fluidic pathways 212, so as to enable selective interconnection of the various components of the growth and harvesting. Although ozone has been illustrated as the sterilant, it is within the purview of the invention to utilize any alternative equivalent means of sterilization which is useful in the process environment, illustrated by, albeit not limited to steam and ultraviolet (UV) light.

With reference to FIGS. 3A, 3B and 3CA, a method of culturing microalgae in which the reactor vessels are filled with nutritive medium and a starter microalgae culture (inoculum) and exposed to sufficient light to allow the microalgae to grow at a rate such that each bioreactor may be harvested in full every 24-48 hours; or other time frame depending on the needs of the strain, will be further illustrated. This illustration depicts a closed system design, wherein everything that enters the growth stage must be controlled. Water and nutrients are coming from the sterile firewall vessel assembly (as illustrated in FIG. 2A) and the growth tank vessel assembly 202 is under positive pressure so no ingress from the surrounding environment occurs, thereby allowing a sterile environment to be maintained by keeping any airborne organisms from contaminating the culture. This allows for air to vent from the system, as oxygen produced by the algae must escape otherwise it would negatively affect algal biomass growth.

Referring to FIGS. 3A and 3B, the components of a standard growth tank vessel assembly 202 are more particularly illustrated. It is noted that the basic reactor vessel assembly 202 is designed around a standardized profile that fits light panels height and width as efficiently as possible.

Growth tank vessel assembly 202 is an illustrative, albeit non-limiting embodiment of a reactor vessel in accordance with the invention, and will be further described herein. The bottom of the growth tank vessel assembly 202 contains one or more bubblers 220 connected to a high-efficiency particulate arrestance or HEPA source of filtered air (not shown) sufficient to operate the bubbler in which bubbles produce currents which circulate the media and microalgae. The airbases or bubblers are used alternatively in the vessel in order to provide biomass gyration inside the tank allowing for maximum venting as well as exposure to light provided by the light panels. Ozone can be delivered using a closed loop device including a Venturi tube and a water pump (not shown). As further illustrated in FIG. 3C, a light source formed from a plurality of thin and substantially flat light guides 224 powered by LEDs are arranged vertically in the vessel 202, preferably in arrays defined by a pre-notched comb-like structure 226 (more particularly illustrated in FIG. 6) to maximize light distribution and illumination surface.

Figure 6:
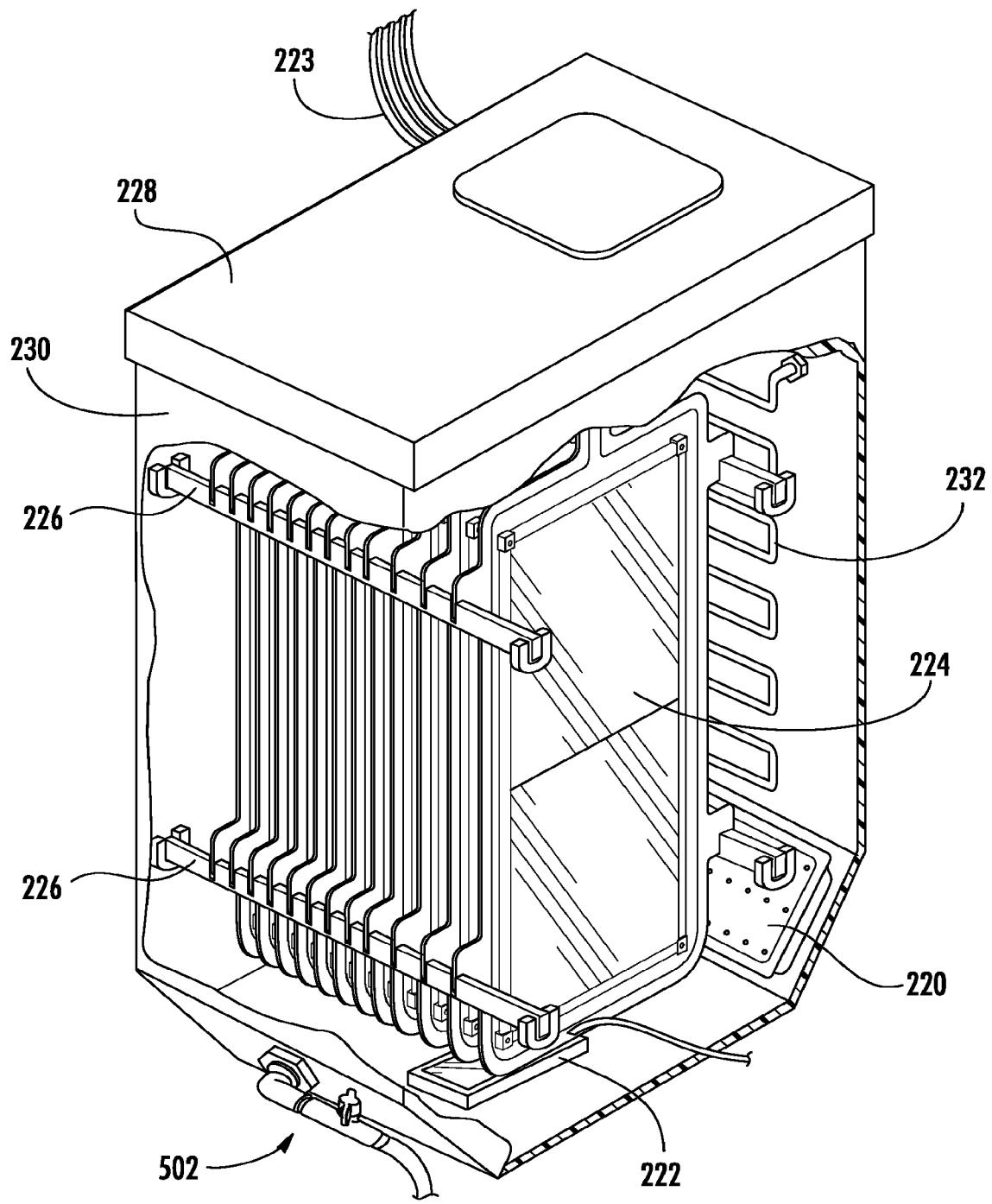
FIG. 6 illustrates a cut-away view of an algal growth assembly including oscillating air bubblers for enhanced turbulence, aeration and flow across the light guides, thereby providing optimized photon flux.
Figure 7A:
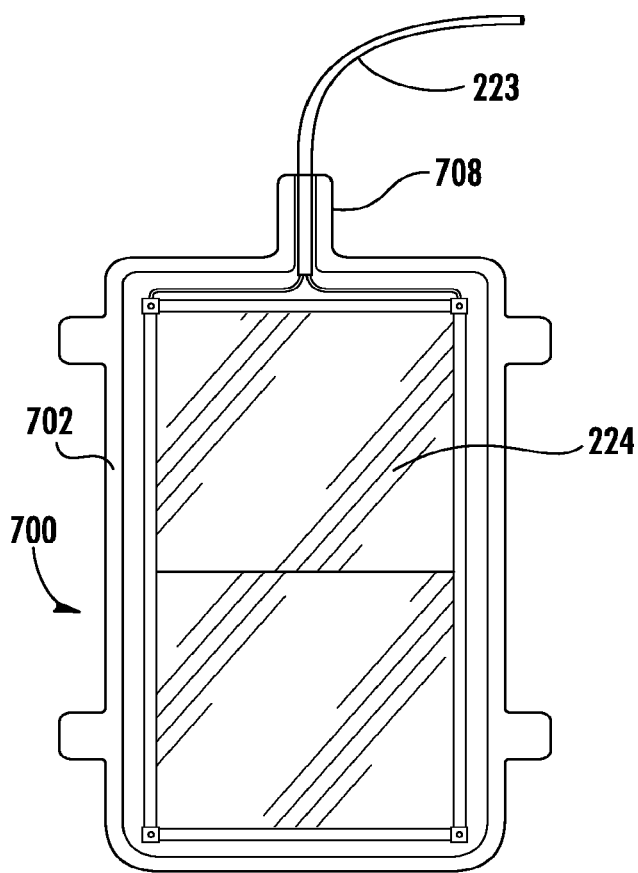
FIGS. 7A, 7B, 7C, and 7D illustrate a plan view (7A), side cross-sectional view (7B), and exploded view (7C) of a typical edge-fed light panel assembly, as well as a sectional view (7D) of a heatsink.
Figure 7B:
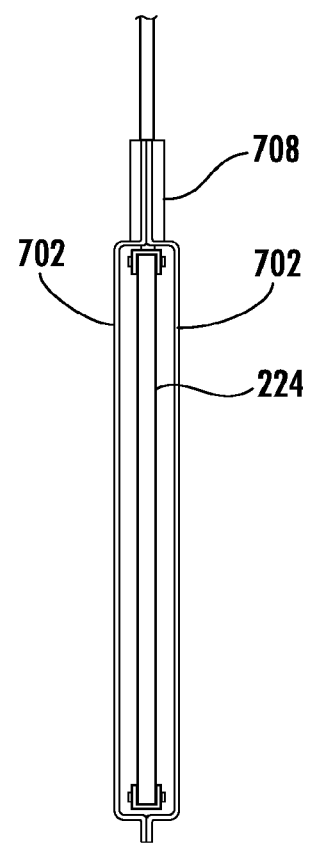
Figure 7C:
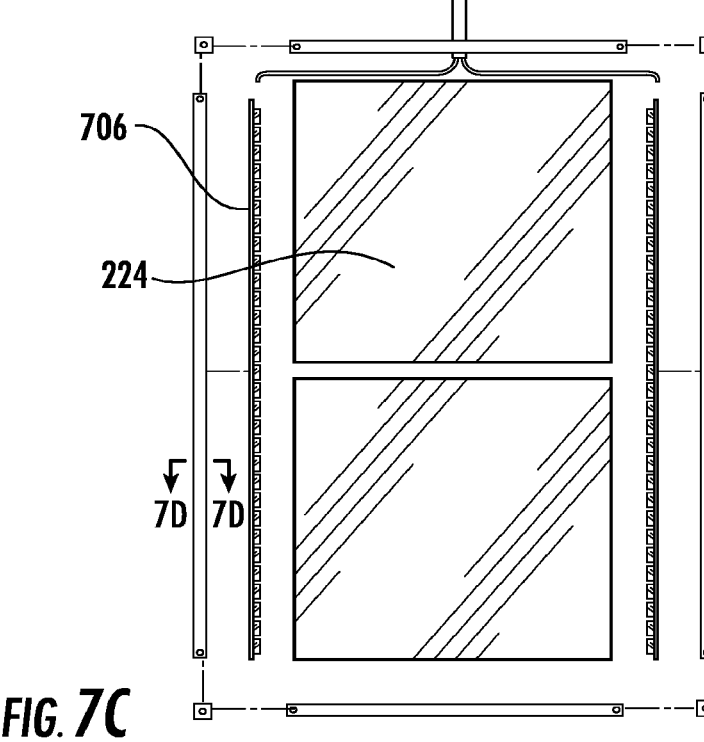
Figure 7D:
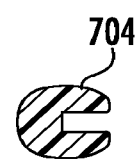

Power is provided to the light panels via cables 223 (FIG. 6). The structure of the growth tank vessel assembly 202 is characterized by a top or cap 228 (purposely left out for clarity, but shown in FIGS. 4 and 6), which is designed to be positioned in a juxtaposed and spaced-apart relationship with the main casing of the vessel 230 in order to allow the escape of oxygen and air and to induce a positive pressure to prevent unwanted entry of extraneous material. The rack of spaced-apart LED light guides 224 are positioned below the top portion 228. Controlled injection of $CO_2$ via bubbler 222 assists in maintaining optimal growth parameters. Movement of the algal biomass is induced by ingress of air from bubblers 220. Temperature is controlled using stainless steel coils 232 that are mostly inert to ozone, chemicals, algal biomass and water (fresh and salt). A cooling/heating media is circulated through the coils 232 in order to maintained the desired thermal conditions optimal for the microalga strain grown.

In an embodiment, the light guides may utilize a MICROLENS™ type of optic, available from the Rambus corporation, which distributes the edge-fed LED light uniformly from the surface of the light guide. Such light guides generally include a light emitting panel member, a light transition area located at one of the ends of the light guide, and at least one light source mounted to the light transition area.

The term "biomass" as used herein and in the claims generally refers to any biological material. Examples of a "biomass" include photosynthetic organisms, living cells, biological active substances, plant matter, living and/or recently living biological materials, and the like. Further examples of a "biomass" include mammalian, animal, plant, and insect cells, as well as various species of bacteria, algae, plankton, and protozoa.

It should be noted that, as used in this specification and the appended claims, the singular forms "a," "an," and "the" include plural referents unless the content clearly dictates otherwise. Thus, for example, reference to a bioreactor including "a light source" includes a single light source, or two or more light sources. It should also be noted that the term "or" is generally employed in its sense including "and/or" unless the content clearly dictates otherwise.

The term "about" or "approximately" as used herein means within an acceptable error range for the particular value as determined by one of ordinary skill in the art, which will depend in part on how the value is measured or determined, i.e., the limitations of the measurement system. Where particular values are described in the application and claims, unless otherwise stated, the term "about" means within an acceptable error range for the particular value.

In order to optimize the disclosed embodiments for maximum commercial scale production, certain basic criteria were developed:

I. The bioreactor must be capable of producing biomass at large commercial scale;

II. The bioreactor must have a small footprint therefore eliminating the use of large open pools of networks of closed bioreactor tubing and bags;

III. The bioreactor must be usable independent of climate and geography;

IV. The bioreactor must achieve a very high algal biomass density equal to or greater than currently accepted industry standards (0.5-1.0 g/l dry weight (DW);

V. The bioreactor must encourage optimal microalgae growth for very efficient use of the space and be commercially viable;

VI. The bioreactor should allow for the controlled semi continuous harvesting of biomass;

VII. The bioreactor must significantly reduce/eliminate the ability of contaminants and pollutants to impede or retard the growth of biomass;

VIII. The bioreactor must significantly reduce the ability of contaminants and pollutants to impede the biomass harvesting process; and IX. The bioreactor must be microalgae agnostic and be adaptable to any species of microalgae or light dependent microorganism.

In order to accomplish these basic criteria, it became evident that the rules governing the parameters for development and growth in the various embodiments would have to depart from the conventional algal growth criteria, and follow a unique set of guidelines and precepts. Among these were the concepts of:

1) Taking the light to the algae;
2) Taking the algae and light to water;
3) Providing a highly controllable and replicable growth environment;
4) Providing high levels of control;
5) Designing for cost effective volume manufacture;
6) Designing for semi-continuous and/or steady state production;
7) Adapting the technology to be biology driven;
8) Designing the systems for deployment in any environment;
9) Designing the systems to operate as a core platform technology; and
10) Developing a unique collaborative business model.

Utilizing these basic concepts make it possible for us to develop embodiments which enable a commercially viable solution for the growth of photosynthetic organisms capable of delivering high yields from a universal approach adaptable to any biologically suitable media or light dependent organism, that could be used anywhere in the world regardless of external lighting or environmental conditions. In order to accomplish this, specific design parameters have been identified for assisting in achieving optimal efficiency and scale-up capability. These design parameters include, but are not limited to:

I. Allowing for adequate mixing to provide suitable momentary light/dark cycles to the cells during the illuminated part of the cycle and avoid gradients and bio-fouling;

II. Providing high mass-transfer capacity to efficiently supply $CO_2$ and prevent $O_2$ buildup;

III. Providing a high surface-to-volume ratio (S/V) of light to increase cell concentration and volumetric productivity;

IV. Enable temperature control at or near the optimum temperature for the cultivated organism;

V. Provide accurate control of nutrients and environmental factors: light intensity, temperature, pH, $CO_2$, and nutrients, such as calcium, magnesium, phosphorus, nitrogen, iron and micronutrients.

VI. Allow for a controllable and predictable harvesting regime to maintain the optimal population density for the cultivated organism;

VII. Allow appropriate light management to reduce photo-inhibition; and maximize photosynthetic efficiency; and reduce photo-limitation.

VIII. Significantly reduce the ability of external factors, pollutants and contaminants to impede or reduce the growth of the cultivated organism.

Utilizing these parameters an environmentally controlled tanking system was developed in order to be able to generate enough biomass at ultra-high density exceeding the industry standards of 1 g/l DW, preferably more than 1 g/l DW, and most preferably at least 5 g/l DW and above, in a small footprint.

This allowed for the use of mass produced components to create a system which achieves the desired efficiencies. This avoids resorting to specially engineered components and their associated higher costs. The use of known systems were either too bulky, required too much space, were not controllable for environmental factors and/or were inherently inefficient and not suitable for commercial use.

These further allowed for the ability to potentially produce large volumes of such photo-bioreactor systems, as plastic tanks are readily available, come in multiple sizes and configurations, are cheap, and easily customizable to specific needs.

In order to maximize space usage three strategies can be used:

I. honeycomb vessel disposition
II. vertical racking system, or
III. continuous flow tanking system With reference to FIG. 4, an engineering drawing of a basic module 202 is provided, along with the associated controls necessary for operation. Air is provided by a blower 234 and controlled through a series of valves and flowmeters in order to deliver the right amount of air through the bubblers 220 in an alternative fashion, so as to insure that biomass movement is homogeneous. Controlled solenoids 236 allow for air to alternate. A bypass system 248 is designed in order to limit any water backflow as well as provide a smooth transition when main aeration is transferred from one bubbler to another. The tank temperature controlled designed is shown where a water cooling device 238 (a water heating system could also be added depending of the conditions) cools water tank reserve. The water from this tank is circulated through the coils 232 located inside the tank. Temperature in the tank is measured 242 as well as the temperature in the cooling water reserve 244 and monitored using a controller 246. A pH probe 248 is also used in the tank. pH is controlled using a $CO_2$ bottle 106 regulated by a solenoid 236 by the controller and injected inside the tank using a fine diffuser 222. Finally, light guides 224 are controlled using an LED driver system 240 that can control the light intensity inside the tank.

Biomass flows through the process, limiting residency time to a minimum, favoring the highest possible productivity and limiting contamination impact.

Everything is tailored to optimize and protect the growth stage that must be preserved and maintained as stable as possible for as long as possible.

One of the caveats of the design criteria is scalability. The system was originally designed so that it could be easily scaled to grow large volumes of biomass. In order to accomplish this, we settled upon the concept of utilizing basic building blocks built around a 1000-liter volume, which is not tank specific. Each building block can then have a drop-in module of light and aeration that could be added either in a specific vessel, a standard intermediate bulk container (IBC), or a large water channel. The ability to mass produce simple components, reducing the whole core technology to a module consisting of a holding frame, cooling coils, light panels, aeration plenum, $CO_2$ diffuser and control probes is at the heart of the scalable modular design concept.

Optimal selection of the light spectrum is also a critical design parameter as it maximizes energy use and efficiency of the whole system. Plant response varies within the visible spectrum. Micro-algae only need the most effective fraction of the photosynthetically active region (PAR) for any given strain. Judicious use of light emitting diode (LED) technology allow us to provide the desired wavelength at the desired intensity. Optimum photon delivery at the most productive wavelength results in better heat management as most photons are absorbed by the biomass.

An additional novel finding which flowed from our experimentation was the ability to lower power consumption. We determined that, contrary to what one would instinctually believe, enhanced production could be achieved using low power LED light. It was determined that it is possible to utilize less light than had been used before by maximizing photon delivery and irradiance area. This has a direct positive impact on power supply units and permits the option of using DC rather than AC power supplies. This reduces energy consumption drastically, which is of paramount importance as the system is scaled up to commercial volumes.

Coupled with the use of low power LEDs is the parameter of surface area optimization. The light source has been designed to optimize the utilization and efficient distribution of photons produced by low/mid power LEDs. Maximizing light availability to volume of biomass creates a "photic" zone which is as large as possible. We have tailored photon per $cm^2$ delivery using flat light guides, and provided a larger contact area using internal lighting illuminating evenly. We have achieved volume reduction of the light source by using thin light guides, in a simple design, requiring as little volume for the immersed element as possible, by making them as thin as possible. We have also taken steps to waterproof the light panels for long term immersion, and incorporated materials that limit or avoid bio-fouling.

With regard to light optimization, we have elected to utilize a flat light area that optimizes photon delivery. We target a volume occupancy of the lighting element at 10% or less of the overall photobioreactor (PBR) volume. This allows for maximum light penetration by increasing exposure. We further increase efficiency by direct immersion as all photon are delivered to biomass. This arrangement maximizes photon distribution as each LED module produces an excessive amount of photons that need to be efficiently delivered to algal biomass. The use of two sided flat panels provide for significantly greater light efficiency as compared to tubes or strips.

In an embodiment, we have discovered that growth may be optimized by controllable night/day cycles. Internal lighting provides total independence from natural light sources. Any light/dark ratio can be tested (e.g., 24:0, 12:12, 14:10, 8:4:8:4 . . . ). LED technology also allows for rapid flickering in the 50-500 Hz range during the light cycle in order to take advantage of the dark phases of the photosynthesis reaction. Flickering allows us to also reduce energy consumption thereby enhancing efficiency.

As a basic requirement we utilize activated charcoal and HEPA filtering of any air input into the system. We further control total air input as well as air temperature using a combination of cooling tubes, intercoolers, and heat exchangers.

Regarding $CO_2$ requirements, pH variation drives the $CO_2$ delivery; pH above the optimum for the strain will trigger gas delivery. Gas exchange is maximized using a ceramic diffuser that produces 100-400 micron size bubble.

Figure 5:
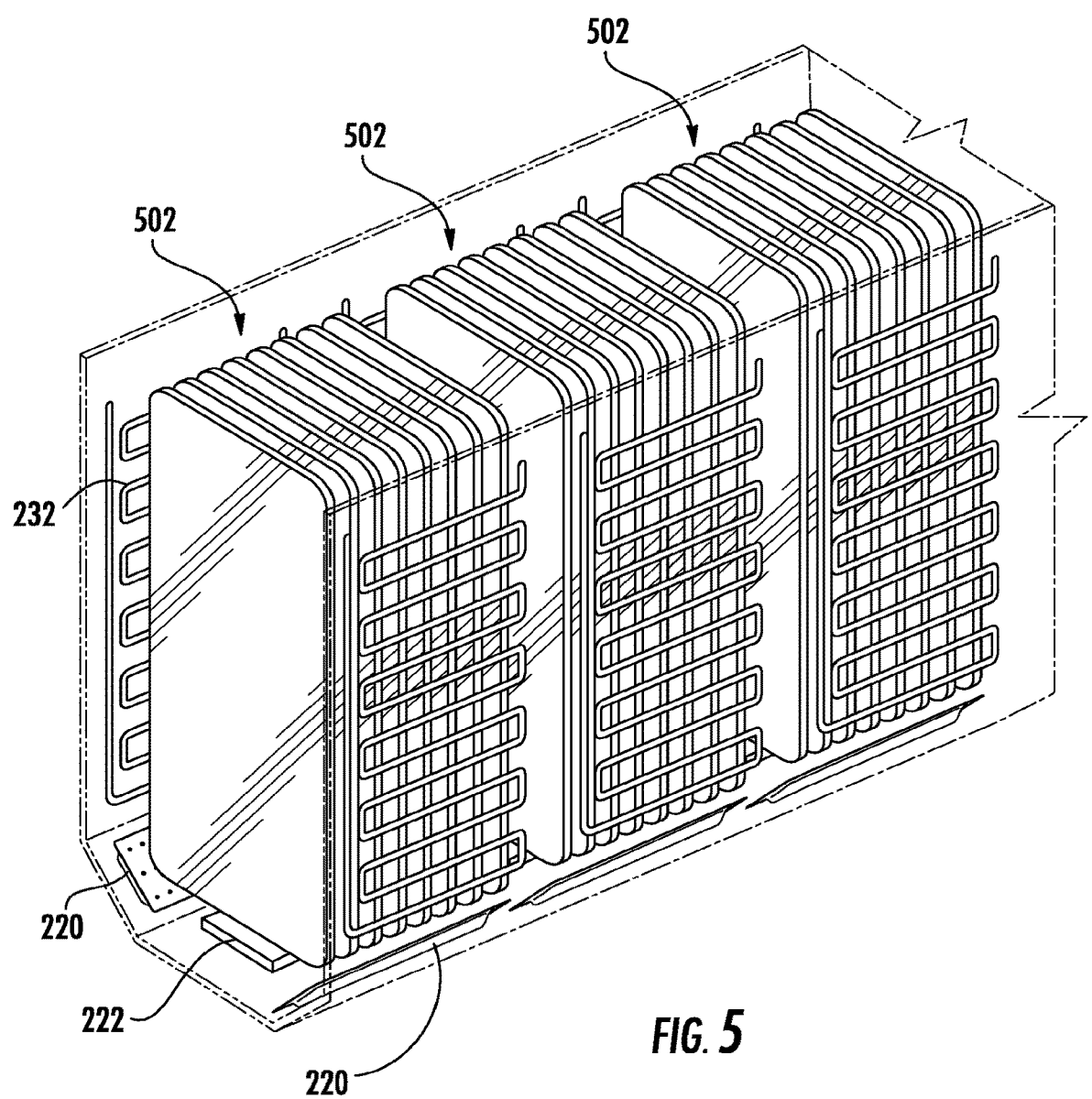
FIG. 5 illustrates scalability of design achieved by appending a plurality of basic units, as depicted in FIGS. 3A, 3B and 3C, to scale-up the bioreactor system at will. Please note that spacing between the modular units is merely illustrative, as it is contemplated to append an infinite number of panels, as required, to meet any expected production requirement.

Now referring to FIG. 5, the purpose here is to illustrate the scalable nature of the design where a plurality of base modules 502 can be added in series in a plurality of vessels of different length and arrangement. For illustration purposes, modules are shown slightly separated but these would be a continuum of evenly spaced panels. A lid (not shown) would also be present in order to maintain a positive pressure environment as described in previous figures.

Referring now to FIG. 6, the tank arrangement is depicted in this version of a basic module 502 within a vessel 230. Light panel assemblies 700 are held in place using a comb like system 226 and spaced at a given interval pre-determined for any given alga strain. A lid 228 is in place closing the system similar to a petri dish in order to create a positive pressure and therefore limit any exogenous particle to enter the system. Cooling coils 232, aeration bases 220 and $CO_2$ diffuser 222 as shown, all controlled using a combination of external controllers, probes and solenoid valves (as illustrated in FIG. 4).

Now referring to FIGS. 7A, 7B, 7C, and 7D, an illustrative embodiment of a light panel assembly 700 is shown. A two-sided, light transmitting, vacuum formed case 702 is provided which is assembled in a watertight manner, thereby providing immersion protection for the edge-fed light guide assembly. The edge-fed light guide assembly contains the edge-fed two-sided light guide 224, and at least one light-emitting diode (LED) printed circuit board (PCB) strip 706 (herein the device is illustrated as, albeit not limited to, a dual edge-fed design). The at least one light-emitting diode (LED) printed circuit board (PCB) strip 706 and the at least one edge of said edge-fed two-sided light guide 224 are maintained in juxtaposed relation within heatsink 704. Top and bottom supports allow for maximal contact to be maintained between the LED strips and the light guide 224 to maintain light transmission efficiency. A power cable 223 exits the panel at the top through a neck like structure 708 in order to minimize any water from entering the panel assembly 700. Light emitted from the LED strip(s) 706 passes through a light transition area, which is formed at the interface of the juxtaposition of the LED strip 706 and the light guide 224 and is thereby injected into the double-sided light guide 224 and is uniformly distributed from each side thereof. This insures even distribution of the photons on each side of the two-sided light guide 224.

Figure 8A:
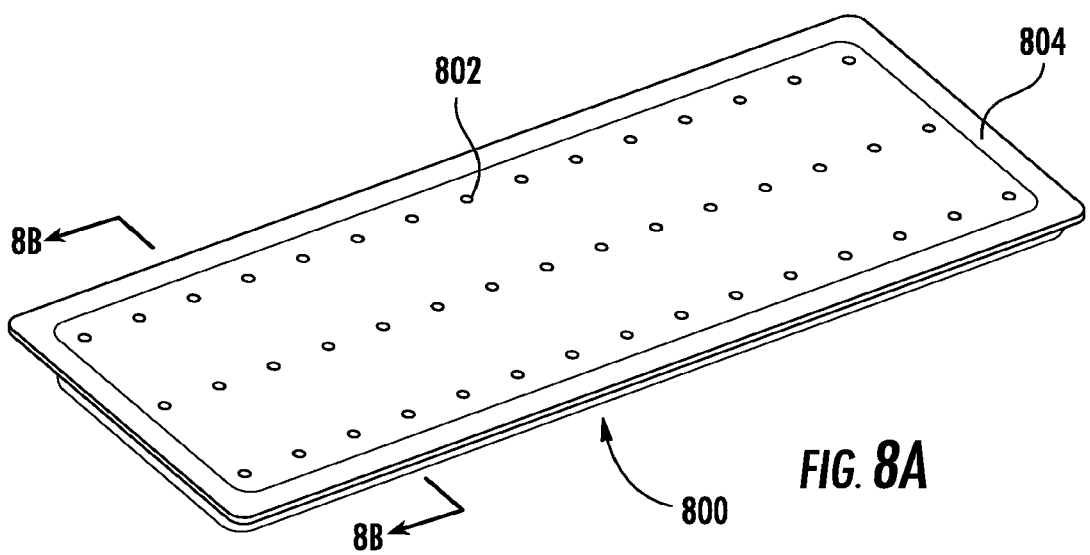
FIG. 8A is a perspective view of an airbase for diffusing air.
Figure 8B:
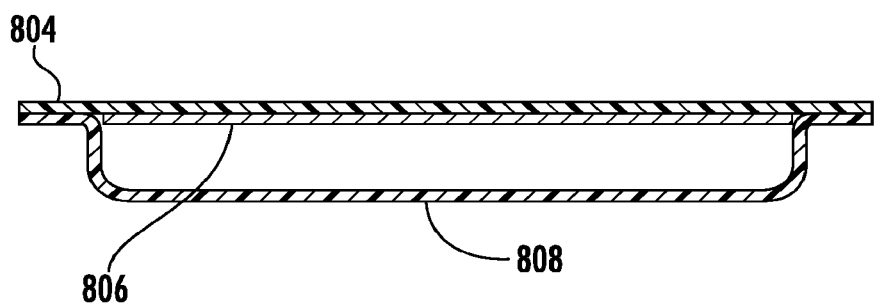
FIG. 8B illustrates a cross-sectional view of the airbase of FIG. 8A.

With reference to FIGS. 8A and 8B, a basic airbase 800 is shown where a plurality of holes 802 are formed within the uppermost face 804 is shown. Hole diameter and number would vary depending upon the degree of biomass growth desired. With reference to FIG. 8B, a cross-sectional view illustrates an optional breathable membrane 806 can be added below the uppermost face 804 in order to limit any biomass entry within the airbase cavity. The lowermost portion 808 is formed so as to leave sufficient volume to be pressurized. The whole airbase 800 is connected to the air system (not shown) using a bulk head fitting (not shown) or any other device that allow air to be efficiently connected to the bubbler.

In an embodiment, algal suspension is optimized. Algal biomass has a tendency to slowly settle over time due to the circular movement generated. Using two oppositely located bubblers that are alternatively switched on, we can also invert the circular biomass movement, therefore limiting any dead spot in a tank or channel, and thereby efficiently limit algal biomass settling as well as bio-fouling.

In an alternative embodiment, the overall principles that allow for the maximization of biomass upon exposure to light in a biologically optimal manner, thereby insuring that the most biomass growth efficiency is attained in a sterile environment, that can be easily scaled up, is illustrated in FIGS. 9A-9F.

Figure 9A:
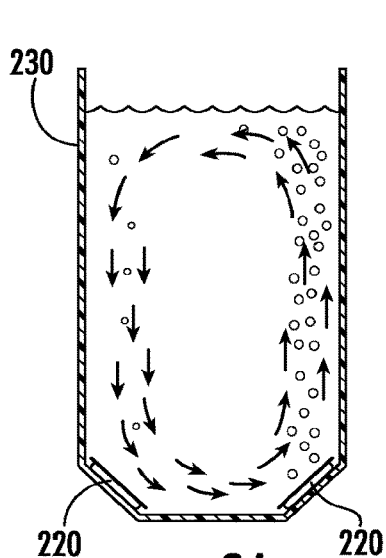
FIGS. 9A and 9B show alternative sectional views, illustrating mixing patterns for biomass contained within a vessel in accordance with the present invention.
Figure 9B:
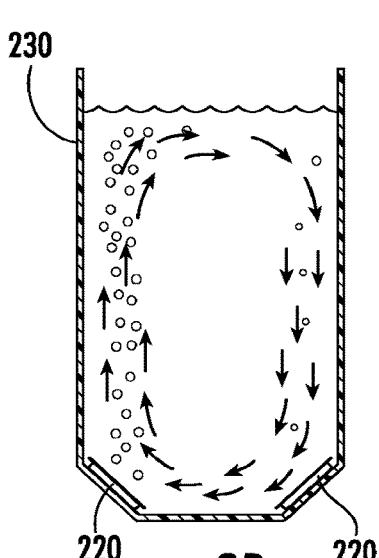
Figure 9C:
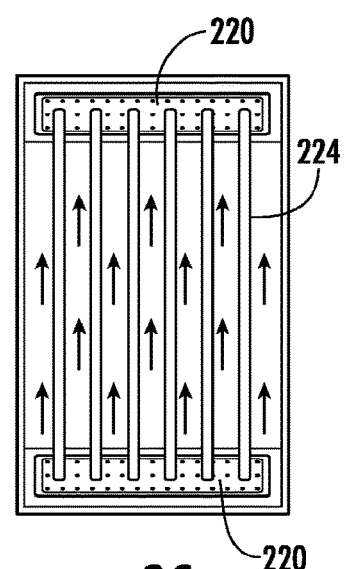
FIG. 9C is a top view of FIGS. 9A and 9B.

With reference to FIGS. 9A, 9B and 9C, it is noted that a fundamental requirement is the need to maintain algae in suspension as well as minimizing any dead spots within the tank. In order to best satisfy this requirement, the instant invention provides for vigorous alternative mixing equivalent to a minimum of 10-30% of a tank volume is required (e.g., a 1000 liter tank will require an air mixing volume ranging from 100 to 300 l/min) to achieve this. In addition to optimal cell suspension, it also allows for venting of oxygen produce by the biomass and general gas exchange. FIGS. 9A-9C illustrate the operation of the device particularly illustrated in FIG. 4. FIG. 9A illustrates initial counter-clockwise rotation from top to bottom as air is bubbled in from a first air bubbler 220 characterized as NO (normally open) in FIG. 4. FIG. 9B illustrates subsequent clockwise rotation from top to bottom as air is bubbled in from a second air bubbler 220 characterized as NC (normally closed) in FIG. 4. FIG. 9C is a top view illustrating the rising of the algae with the air-induced currents on either side of the light guides 224.

Figure 9D:
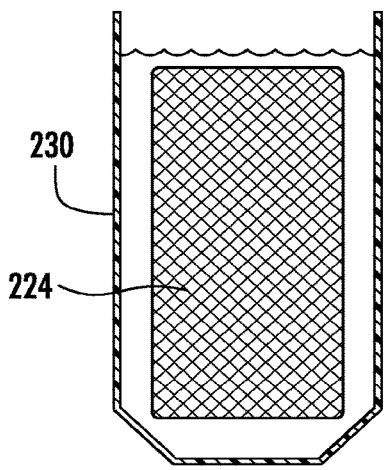
FIG. 9D illustrates a vessel containing a light guide, to show maximization of the photic zone.

Referring to FIG. 9D, a cross-sectional view of tank 230 including light guide 224, is illustrated. This configuration achieves maximal particle transit and light exposure where the homogeneous photon flux irradiates the biomass as evenly as possible by maximizing the photic zone/illuminated area with light panels that are optimized to fit as much space as possible in the tank. This is a very important factor that, combined with optimal biomass flow, increases photosynthetic efficiency.

Figure 9E:
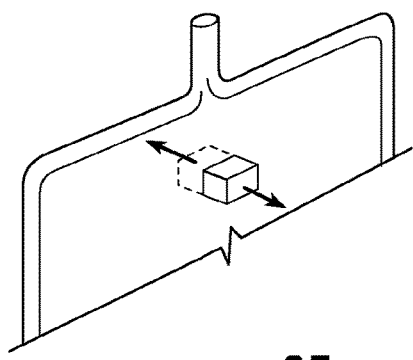
FIG. 9E illustrates a specific portion of a light guide, which is further detailed in a zoomed-in version in FIG. 9F to illustrate the emission of photons from each side of the light guide to maximize biomass growth.

Regarding FIG. 9E, a section of the double-sided light guide is delineated to emphasize the mechanism of uniform light distribution. It is critical to this operation to understand that light distribution is a key part of this whole process as photons delivered by a single LED chip are vastly excessive and need to be distributed as much as possible in order to limit photo-inhibition and maximize biomass growth. As earlier described in FIG. 7, light emitted from the LED strip(s) 706 passes through the light transition area, which is formed at the interface of the juxtaposition of the LED strip 706 and the double-sided light guide 224 and is thereby injected into the double-sided light guide 224 and is uniformly distributed from the surfaces thereof. This insures even distribution of the photons on each side of the double-sided light guide 224.

Figure 9F:
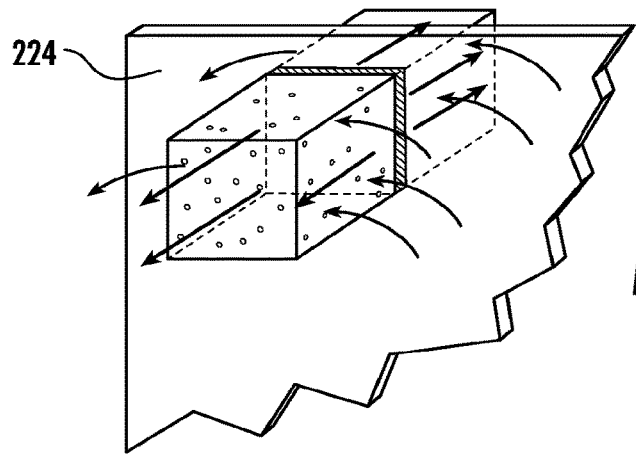

FIG. 9F is a schematic view of the section delineated in FIG. 9E, which illustrates the balance that has to be achieved where optimal biomass movement allows for algal particle transit across a large area of light. Photon flux provided to the biomass is optimized so no photo-inhibition is induced that will impede growth but at the same time enough photosynthesis is achieved to allow for biomass synthesis and cell division. Moreover, oxygen waste is rapidly eliminated in order to avoid cell respiration, which will result in a stoppage of the photosynthetic process all together. The controlled environment provided by the current system allowing for maximal homeostasis and consistency in a semi-continuous growth system.

$$\text{Optimal algal biomass growth} = (\text{Cell concentration} \times \text{cell size})^{light\ penetration} + (\text{biomass flow} \times \text{air flow})^{algal\ photosynthesis/light\ exposure} + (\text{waste management} \times \text{sterile process} \times \text{environmental control})^{system\ homeostasis}$$

The proposed system addresses controls and manages all these key fundamentals. Optimal light delivery is achieved by having the panels 224 immersed in the vessel, thereby providing the utmost nutrient control, such that it is no longer a limiting factor.

Figure 10D:
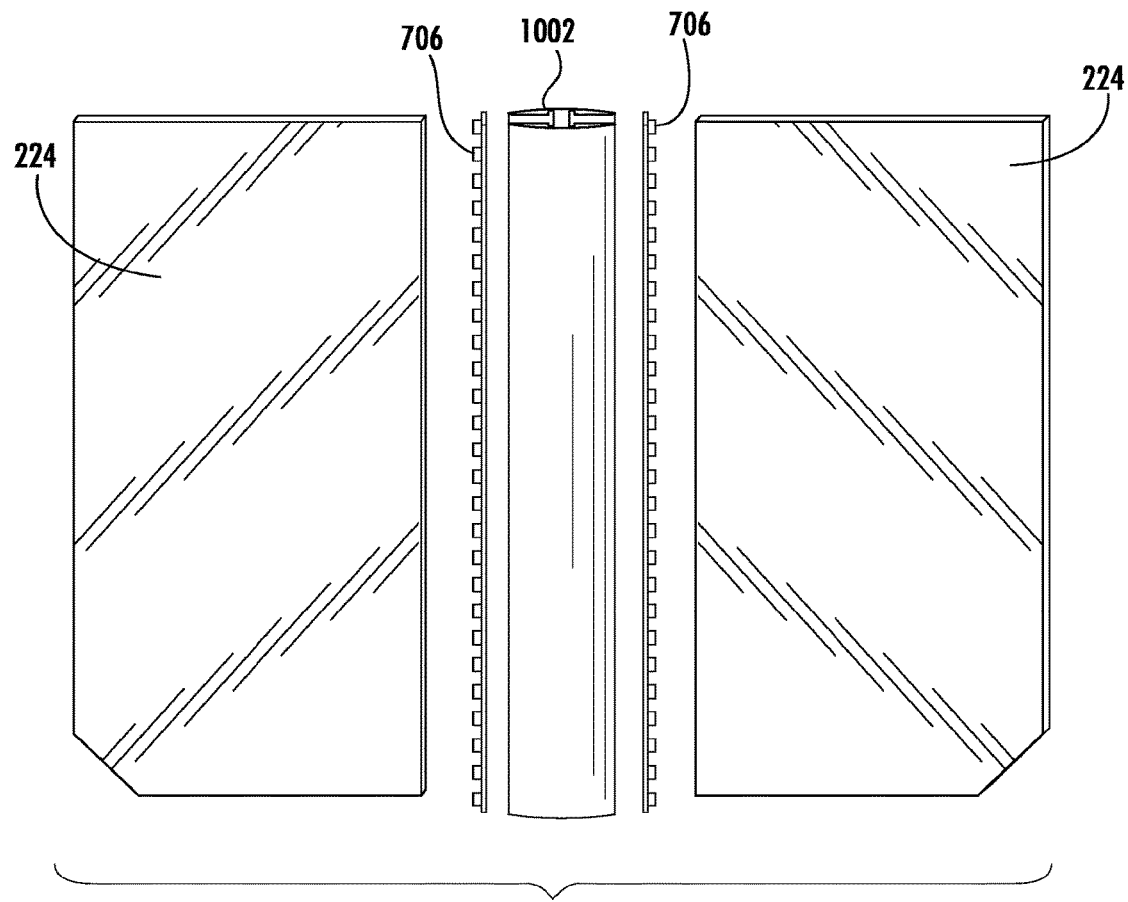
FIG. 10D is an exploded view of the light guide of FIGS. 10A and 10B.
Figure 10E:
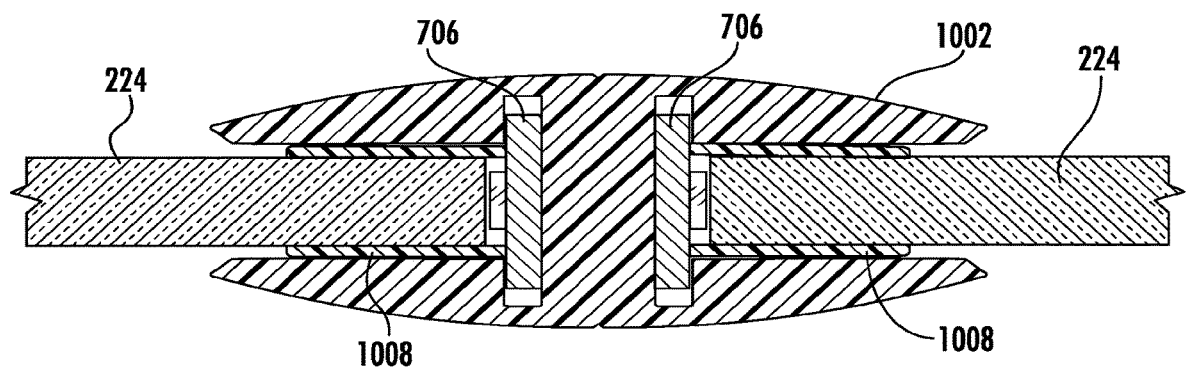
FIG. 10E is a top view illustrating joinder of the LED printed circuit boards and light guides via a central heat sink.

Referring to FIGS. 10A, 10B, 10C, 10D and 10E, this figure illustrates another possible iteration of a light panel where the LED strips are located in a central spine/column allowing the light guide to be shaped optimally to fit a vessel in order to further increase the photic zone and improve on algal growth as well as simplify panel positioning using a build spacing system. FIG. 10A represents an overall view of a central column panel 1000 built on the same principle of the panel described in FIG. 7. In this case, the LED PCB strips are located centrally and inject light in the light guides 224 on one side only. In FIG. 10B, a side view shows the central column light panel 1000 encased in a vacuum formed transparent plastic casing 1004 where only one side is formed. FIG. 10C is a view illustrating where the panels 224, encased by assembly 1004 are shown inside the vessel where they are maintained in position by built in combs/spacers 1006. The panels 224 and encasing assembly 1004 are designed to occupy as much space as possible in order to increase the photic zone. FIG. 10D is an exploded view of the central heat sink 1002 LED strips 706 and light guides 224. Lastly, FIG. 10E is a cross-sectional view of the central guide/heatsink 1002, LED strips 706, light guide 224 and reflective material 1008 is shown as a possible illustration.

As an alternative embodiment, it is within the purview of the present invention to utilize water compatible lenses, and waterproof LED strips which would allow the light panel assemblies to be utilized without the requirement of a waterproofed vacuum formed case, as illustrated.

It is further within the purview of the present invention to utilize an alternative waterproofing device, such as a vacuum bag, as an equivalent embodiment.

The next parameter that may be optimized in various embodiments is nutrient delivery. Steady state of the culture when operating the reactor semi-continuously requires that nutrients be perfectly dosed so at most 0.5-3% are left at each harvest time (97-99.5% consumed in between harvests).

At steady state, every alga strain will consume each nutrient at a given rate assuming a given starting concentration, optimal mixing and light amount in a very reproducible and stable manner.

Nutrients, inclusive of calcium, magnesium, nitrogen, iron, phosphorus and various micronutrients, are dosed utilizing an optimized nutrient recipe. Semi-continuous cultivation requires that each alga strain has its specific nutrient recipe. Each refresh should supply just the right amount of nutrients so no starvation or accumulation occurs. This leads to the creation of a bento box that provide all the necessary nutrients between each refresh where optimal growth is obtained in specific stable conditions.

EXAMPLES

Algal Biomass Process Control Protocols and Parameters

Each type of bioreactor, alga strain, and end usage for the algae require specific methods and standard operating protocols to be tailored and optimized. The following protocols intend to provide an overall understanding of the process and key steps necessary to run a tank-based photo-bioreactor in accordance with the present invention.

The construction and arrangement of the working environment has been designed to limit, to the utmost extent possible, any external contaminations, therefore good manufacturing practices (GMPs) and clean room operation (HEPA filtered, operator wearing protective equipment) are used as many water and airborne parasites can interfere and contaminate algae being grown for considerable amount of time in a semi-continuous method unlike a batch system.

Growth Phase: Cylindrical and IBC Tanks

Morning Setup as an Operator would Walk in:

Firewall tank is already filled with water and nutrients (except autoclaved micro-nutrients that are stored at 4° C.) from the day before that have been mixed all night (see table below). This also allows for the tank to be temperature balanced.

Growth tanks are on a 12 hours light, 12 hours dark cycle. The pH is controlled during the light hours only using a monitoring and control system (e.g., Neptune Apex system) to never exceed 7.55 (when the $CO_2$ is injected). $CO_2$ injection is stopped when a pH of 7.50 is achieved. No $CO_2$ is injected when the lights are off and pH is allowed to raise.

$CO_2$ delivery is performed using a 30×10 cm wide fine ceramic diffuser at 1.7-2.3 bar producing micro bubbles of 100 to 400 micrometer diameter in size. A normally closed electrically controlled solenoid regulates the gas injection. The electrical plug that controls the solenoid is managed by the Apex system as described above.

Aeration to the tanks is provided by a regenerative blower delivering approximately 10%-30% of the total tank volume per minute of air continuously on a 24/7 basis. This is controlled using a rotameter and a ball valve.

Typically, this whole harvesting process would be initiated promptly after the lights turn on in the growth tanks and end 30 to 60 minutes later at most. This limits biomass disturbance of the growing micro algae to a minimum.

Process:
1. The night prior, the water pump/Venturi injector/ozone generator system connected to the firewall tank is turned on. The firewall tank is ozone treated to an ORP reading of at least 900 for a duration of 5 minutes. Ozone flow of 4 to 5 liters per minute at 20 PSI is used at a rate of approximately 30 grams of ozone per hour (Atlas 30 ozone generator). Once the correct ORP reading is achieved in level and duration, the ozone is switched off and the firewall tank is allowed to vent the remaining ozone overnight as it rapidly decays once generated (15-30 min half life in water).
2. Sterile micro-nutrients are added to the firewall tank and allowed to mix for 5 minutes.
3. Meanwhile, growth tanks are serially harvested 20-25% into the harvesting tank.
4. Using the water pump used in 1 or by gravity alone, nutrient rich water is now transferred to each growing tank in order to restore the volume of biomass. All tubes containing the media having been sterilized in the ozone process the day before.
5. The empty firewall tank is rinsed and immediately filled with fresh water to a volume equivalent to what will be used at the next cycle (next 24-48 hr), nutrients are added (except micro-nutrients) and allowed to mix. The tank is ozone sterilized at this point in order to limit the growth of any unwanted organisms as described in 1.

TABLE 1

Media recipe used to grow *Nannochloropsis* sp.

| | Concentration (mM) |
|---|---|
| Nitrogen NaNO$_3$ | 4.0 |
| Phosphorus: Na$_2$HPO$_4$ | 0.2 |
| Marine salt | $0.51 \cdot 10^3$ |
| Micronutrients | |
| Zinc: ZnCl$_2$ | $2 \cdot 10^{-3}$ |
| Manganese: MnCl$_2 \cdot 2H_2O$ | $2 \cdot 10^{-3}$ |
| Molybdenum: Na$_2$MoO$_4 \cdot 2H_2O$ | $2 \cdot 10^{-3}$ |
| Cobalt: CoCl$_2 \cdot 6H_2O$ | $2 \cdot 10^{-4}$ |
| Copper: CuSO$_4 \cdot 5H_2O$ | $2 \cdot 10^{-4}$ |
| Iron: C$_6$H$_5$FeO$_7 \cdot 5H_2O$ (Ferric citrate) | 0.04 |
| EDTA·Na | $46.4 \cdot 10^{-3}$ |
| Vitamins | $mg \cdot L^{-1}$ |
| Thiamine | 0.07 |
| Biotin | 0.01 |
| Vitamin B12 | $6.0 \cdot 10^{-3}$ |

Table 1 describes the various chemicals used to grow *Nannochloropsis* sp. Depending of the usage of the biomass, various grades can be used ranging from laboratory to fertilizer grade. Micronutrients are prepared separately autoclaved and then filter-sterilized vitamins are added. EDTA is used as a chelating agent that prevents precipitation. Micronutrients are added after the firewall tank is ozone sterilized as indicated above.

Harvesting Phase

There is a plethora of harvesting methods that can be used depending upon the final usage made of the algae. Since the algae is independently located from the growth tanks, filtration, flocculation, centrifugation or any other harvesting system can be safely used without in any way affecting or endangering the semi-continuously growing algae.

*Nannochloropsis* sp. was successfully harvested as a paste using a GEA Westfalia SC6 continuous centrifuge using the following conditions:
  rotor speed: 10,000 rpm
  discharge every 12 minutes
  intake biomass flow of 25 liters/minute This produced a concentrated paste at 25-50% biomass. Due to the flexibility of the centrifuge, final concentration can be tailored to the end usage of the biomass even for such a small size micro-algae specie.

Results
Baseline in 0.91 bottle
  12:12 light/dark cycle
  5 W of illumination @ 660 nm, 500×10$^6$ cells per ml, equivalent to 5.55 W/liter 9:3 light/dark cycle
  5 W of illumination @ 660 nm, 150×10$^6$ cells per ml, equivalent to 5.55 W/liter
250 Liter Tank
  12:12 light/dark cycle
  60 W of illumination @660 nm, 150×10$^6$ cells per ml, equivalent to 0.24 W/liter
    23.times. less light per liter of biomass results with only 3.3× less biomass, making it 7.times. more efficient than baseline.
  130 W of illumination @660 nm, 250×10$^6$ cells per ml, equivalent to 0.52 W/liter
    11× less light per liter of biomass results with only 2× less biomass, making it 6× more efficient than baseline.
  9:3 light/dark cycle
  90 W of illumination @660 nm, 200×10$^6$ cells per ml, equivalent to 0.36 W/liter
    15× less light per liter of biomass results with 1.3× more biomass, making it 20× more efficient than baseline.

Continuously Operating Channeled Tank Construction

This would be the potential protocol used to run a "river" style tanking. In this scenario, the growth phase is performed inside a tank consisting of channels that are lighted using flat panels or dark in order to reproduce the light dark cycle which is accomplished in a static manner in a cube. As for the upstream and downstream peripheral elements such as firewall and harvesting tanks, they remain very much the same as for a cube base system. The system described herein is a virtual 5 m$^3$ river but larger system would be using virtually identical methods with only slight adaptations. The current scenario describes a river used to produce a set amount of biomass every cycle where 20% of the river is harvested and 20% is replaced by sterile nutrient rich water.

Initial Cleaning and Seeding

Prior to seeding a river based tank, it will need to be extensively cleaned and sterilized. All river walls and aeration element will be disinfected using bio-compatible detergent, bleach and 70% ethanol. Copious amount of water will be used to rinse out the tank and the elements present inside and dried out prior to filling the whole river with water. As a reminder, the tank will be kept in an enclosure where HEPA filtering is used in order to limit airborne contaminations.

Once the tank is cleaned, it is filled with sterilized nutrient rich water (UV and/or ozone). At this stage, the various elements of the river are switched on (regenerative blower, Apex control system, lights, cooling systems, pH and temperature probes, CO$_2$ delivery, peristaltic circulating pumps . . . ) and the river is subsequently seeded.

The seeding concentration will vary between algae strain and the overall timing necessary to get the river up to capacity in a commercial scenario. In the case of a small 5 m$^3$ river tank, a 1 m$^3$ algal seed can be used directly from a growth cube/rack and then the river is circulated in a close loop for a number of cycle so it reaches the desired biomass concentration. Alternatively, the 5 m$^3$ river can be immediately seeded to capacity using four 1 m.sup.3 cubes and completed with 1 m$^3$ of nutrient rich water equivalent to a 20% refresh. In this scenario, the algae will be ready to immediately be harvested. In order to limit algal perturbation in its cycle, algae would be transferred in the dark phase, 3-4 hours after the lights would have been switch off in a cube system. Algae that would be located in a light area of the river would be ready to grow while algae present in the dark would have only a slightly extended dark phase.

Growth Phase and Continuous Harvest

Once the river is at capacity, a continuous amount of biomass is harvested. In this case 20% daily equivalent to 1 m$^3$/day or 41.67 l/hr. Here, two peristaltic pumps are at work. One with two heads is harvesting 695 ml/min into a harvesting tank from the end of the river while replacing the algal biomass by 695 ml/min of sterile nutrient rich water fed from the firewall tank at the beginning of the river. At the same time, a second peristaltic pump is transferring 2.78 l/min of algal biomass from the end of the river to the start of the river. Indeed, the river is not a closed loop but rather a U-shape tanking system with controlled entry and exit.

Monitoring is performed by using the telemetry in place (video cameras, Apex control systems) that allows an operator to constantly monitor the river health and control as well as direct visual inspections in order to make sure that all systems are operational (light panels, solenoids, probe calibration). Moreover, sampling is performed from set points in the river in order to monitor that all processes are performing appropriately.

A fresh firewall tank is made every day and the biomass in the harvest tank vessel is used. In a typical system, two firewall tanks and two harvest tanks would be used in order to allow for a continuous operation.

Depending on the purpose and use of the biomass, it could be used as is for fish feed or concentrated using centrifugation or filtration. The algal paste can then be refined to extract molecules of interest using a wide range of processes that goes beyond the scope of this process depiction.

Comparisons of Cube Versus River Process Protocols

While the tank and river system have the same fundamental concept of bringing light to the algae, the key difference is the continuous flow of the biomasss. In the latter, rather than a static system like the cube where the algal biomass is in a cyclic mode with the conditions constantly changing at any given time of the day (increase in cell count, nutrient consumption, light on/off) until the next harvest and refresh, the river is, in effect a steady state process where conditions at any given point remain constant at all time.

Briefly, algal biomass treks through a fully aerated channel for a given time where it is initially exposed to light in a pH controlled environment with $CO_2$ injected through diffusers located at preset intervals approximately 0.5-1.5 meters apart. $CO_2$ is injected when probes sense a rise in pH controlling the activation of a solenoid valve in a similar fashion as for the cube design. Concomitant with this fine control, $CO_2$ enriched air can also be used (e.g., industrial cement factory emission, sewage sludge aeration basin emission). When sufficient light exposure has been achieved the algal biomass now arrives in a non-lighted area for a preset time. If multiple light/dark cycle are necessary between harvest, a river can be designed so as to have a series of one or more sections with or without light panels. However, at the end of the river, part of the algal biomass will be set aside for harvest and the remaining portion will be returned to the beginning of the channel. In order to compensate for the lost volume, fresh nutrient rich medium is added upstream at the same rate it is removed downstream.

Dependent upon the usage made of the river, various scenarios are possible. If the intent is to grow biomass, a given percentage (50%-90%) is returned to the river start and the remaining harvested biomass (10%-50%) is being processed (stress stage if necessary, dewatering, chemical extraction). However, if the intent is to clean water (e.g. post-sewage treatment industrial nutrient rich effluents), then most of the biomass is dewatered (concentrate) in order to flow through the cleaned water (centrate). From the biomass paste obtained, a fraction (5%-50%) is harvested as described above while the remaining paste (50%-95%) is mixed with nutrient rich water and used to seed a new cycle of algal growth.

The overall purpose of the river concept is therefore to vastly increase the volume of water, and consequently the biomass being cultured, in a cost effective manner where a cube system would quickly be unable to practically deal with such large volumes. Indeed, while it is possible to perform similar operations in a cube system, the cost of moving the water and the excessive number of cubes would simply make dealing with large volume cost prohibitive. In the case of the river, the water is simply flown through the system using minimal pumping while maximizing efficiency as in the cube system.

Two Phase Algal Growth

Some algae strains (e.g., *Chlorella* sp, *Haematococcus pluvialis*) require two phases in order to produce a specific chemical. The first growth phase is where the algal biomass expands in a nutrient rich medium and is regularly harvested and maintained at a highly productive status as we have described in the cube or river concepts. After harvesting and before dewatering, the second stress phase is initiated. This is typically done by nutrient depletion combined with intense lighting and/or other stress factors. When nutrients are being totally consumed by the algal biomass, this rapidly results in the accumulation of specific chemicals aimed to protect the algae from stress. Many valuable chemicals (e.g., astaxanthin, beta-carotene) can be produced using this approach in very high concentration.

In order to allow for such additional stress phase, we have designed a specific cube racking system that is fed by gravity, thereby allowing the growing algae to be regularly harvested and transferred into stressed cubes where lights remain on 24 hr a day. Depending of the algae strain, stress can be performed for 1 to 10 days in order to accumulate as much as possible of the chemical of interest. After this stage, the algae are dewatered, cracked, dried and the chemical extracted using processes typically used in the field (e.g., supercritical $CO_2$ extraction, mechanical extraction, large scale chromatography, distillation, solvent extraction).

A rack is typically set up with one or more firewalls at the top, 3 to 5 growth tanks in the middle and 2 to 6 stress tanks at the bottom. Firewall and growth tank numbers are dependent upon the harvesting rate while the number of stress tanks is dependent on the duration of the second stressing phase. All tanks are fluidically connected in order to allow for liquid transfer between them which is performed by gravity in this case. All tubing can be isolated and sterilized in order to avoid any possible waterborne contamination.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed:

1. A method for cultivating a photosynthetic microorganism, comprising: providing a cultivation system comprising a firewall vessel, at least one growth vessel, at least one bubbler or gas-diffuser, a light panel, and a sterilizing material configured to sterilize fluid originated from the firewall vessel; placing a fluidic loop into a first state that places the firewall vessel into fluid communication with the sterilizing material while being in fluidic isolation from the at least one growth vessel of a growth stage; communicating a fluid from the firewall vessel within the fluidic loop in the loop's first state so as to contact the fluid with the sterilizing material and give rise to a sterilized fluid circulated within the fluidic loop and the firewall vessel; placing the fluidic loop into a second state that places the firewall vessel into fluid communication with the at least one growth vessel of a growth stage; introducing the sterilized fluid from the firewall vessel to the at least one growth vessel; introducing a nutrient and a photosynthetic microorganism to the sterilized fluid; in the at least one growth vessel, illuminating the photosynthetic microorganism with a light panel immersed in the at least one growth vessel; and cultivating the photosynthetic microorganism so as to produce an amount of biomass.

2. The method of claim 1, further comprising operating a bubbler configured to provide airflow into the at least one growth vessel so as to circulate the fluid disposed within the at least one growth vessel.

3. The method of claim 1, further comprising operating at least two bubblers so as to give rise to alternating circulation of the photosynthetic microorganism in the fluid disposed within the at least one growth vessel.

4. The method of claim 1, further comprising communicating the photosynthetic microorganism from the at least one growth vessel to a stress vessel in the cultivation system, and further (a) subjecting the photosynthetic microorganism in the stress vessel to a nutrient level that differs from a nutrient level in the at least one growth vessel, (b) subjecting the photosynthetic microorganism in the stress vessel to an illumination level that differs from an illumination level in the at least one growth vessel, or both (a) and (b).

5. The method of claim 4, wherein the subjecting the photosynthetic microorganism to an illumination level that differs from an illumination level in the at least one growth vessel comprises illuminating the photosynthetic microorganism with a light panel immersed in the stress vessel, the light panel comprising at least one edge-fed light guide.

6. The method of claim 1, wherein the light panel comprises at least one two-sided light array, at least one light-emitting diode (LED) strip, and at least one heatsink, wherein said at least one two-sided light array and said at least one LED strip are maintained in relative position by said at least one heatsink, and wherein light emitted from said at least one LED strip is injected into the two-sided light array and is distributed from each side thereof.

7. The method of claim 1, wherein the illuminating is effected with the light panel immersed in the at least one growth vessel, the light panel comprising at least one edge-fed light guide.

* * * * *